(12) United States Patent
Bai et al.

(10) Patent No.: US 12,183,109 B2
(45) Date of Patent: Dec. 31, 2024

(54) MODELING METHOD AND MODELING DEVICE FOR HUMAN BODY MODEL, ELECTRONIC DEVICE, AND STORAGE MEDIUM

(71) Applicant: BOE TECHNOLOGY GROUP CO., LTD., Beijing (CN)

(72) Inventors: Hua Bai, Beijing (CN); Guang Bai, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 405 days.

(21) Appl. No.: 17/631,572

(22) PCT Filed: Mar. 2, 2021

(86) PCT No.: PCT/CN2021/078656
§ 371 (c)(1),
(2) Date: Jan. 31, 2022

(87) PCT Pub. No.: WO2021/175208
PCT Pub. Date: Sep. 10, 2021

(65) Prior Publication Data
US 2022/0270387 A1 Aug. 25, 2022

(30) Foreign Application Priority Data
Mar. 2, 2020 (CN) .......................... 202010137229.5

(51) Int. Cl.
*G06V 40/10* (2022.01)
*G16H 50/50* (2018.01)
*G16H 70/20* (2018.01)

(52) U.S. Cl.
CPC ............. *G06V 40/10* (2022.01); *G16H 50/50* (2018.01); *G16H 70/20* (2018.01)

(58) Field of Classification Search
CPC ...... G06V 40/10; G06V 10/44; G06V 40/103; G06V 20/647; G16H 50/50; G16H 70/20; G16H 30/20; G16H 30/40; G06T 17/00
(Continued)

(56) References Cited

U.S. PATENT DOCUMENTS

2013/0249908 A1  9/2013  Black et al.
2017/0243354 A1  8/2017  Tafazzoli et al.
(Continued)

FOREIGN PATENT DOCUMENTS

CN       1987879 A  *  6/2007
CN     102298667 A  * 12/2011
(Continued)

OTHER PUBLICATIONS

"3D Human Body Modeling Based on Anthropometric Measurements", Master's Thesis, Nanjing Aero and Space Technology Univerity, p. 7 to p. 44 issued on Mar. 15, 2018.
(Continued)

*Primary Examiner* — Juan A Torres
(74) *Attorney, Agent, or Firm* — HOUTTEMAN LAW LLC

(57) ABSTRACT

Provided are a modeling method and a modeling device for a human body model, an electronic device, and a storage medium. The modeling method includes: acquiring a human body size of the user; performing a scaling process on a standard human body model, to obtain a reference human body model; acquiring a human body image of the user; obtaining sizes of body parts of the user; determining to-be-moved target positions of each reference body surface feature point and the reference bone point of each set of reference control points of the reference human body model; adjusting each reference body surface feature point and each reference bone point of the reference human body model to
(Continued)

the to-be-moved target positions to obtain the customized human body model of the user.

19 Claims, 13 Drawing Sheets

(58) Field of Classification Search
USPC .......................................................... 382/128
See application file for complete search history.

(56) References Cited

U.S. PATENT DOCUMENTS

| 2017/0330375 | A1 | 11/2017 | Chen et al. | |
| 2020/0126295 | A1* | 4/2020 | Mok | G06V 20/64 |
| 2021/0307621 | A1* | 10/2021 | Svenson | A61B 5/7267 |

FOREIGN PATENT DOCUMENTS

| CN | 106419922 A | * | 2/2017 | ........... A61B 5/1072 |
| CN | 107545598 A | | 1/2018 | |
| CN | 107705365 A | | 2/2018 | |
| CN | 108836285 A | | 11/2018 | |
| CN | 108986159 A | | 12/2018 | |
| CN | 109409348 A | * | 3/2019 | |
| CN | 110648394 A | | 1/2020 | |
| WO | WO 2020006961 A1 | | 1/2020 | |
| WO | WO 2020037680 A1 | | 2/2020 | |

OTHER PUBLICATIONS

Hi Die, "Three-dimensional human body modeling based on anthropometric measurements," Master's Thesis, Mar. 15, 2018, pp. 7-44, Nanjing University of Aeronautics and Astronautics, Nanjing, Jiangsu, China.

China Patent Office, CN202010137229.5 First Office Action issued on Jun. 1, 2024.

* cited by examiner

Standard Three-dimensional Human Body Model    Reference Three-dimensional Human Body Model Reference Three-dimensional Human Body Model    Customized Three-dimensional Human Body Model

# MODELING METHOD AND MODELING DEVICE FOR HUMAN BODY MODEL, ELECTRONIC DEVICE, AND STORAGE MEDIUM

CROSS-REFERENCE TO RELATED APPLICATION

The present application claims the priority of Chinese Patent Application No. 202010137229.5 filed on Mar. 2, 2020, the contents of which are incorporated herein in their entirety by reference.

TECHNICAL FIELD

The present disclosure relates to the field of human body model technology, and in particular to a modeling method and a modeling device for a human body model, an electronic device, and a storage medium.

BACKGROUND

With the development of two-dimensional and three-dimensional digital human body technology, more and more industries (such as smart medicine or games) need to provide users with customized human body models to enhance user experience.

In the related art, the human body model is generally generated for the user through manual modeling. This modeling method requires a lot of manual work, and the modeling efficiency is low. Moreover, the human body model generated by manual modeling has a lower matching degree with the user's real body shape characteristic, lacks reality, and cannot significantly improve the user experience.

SUMMARY

In an aspect, provided is a modeling method for a human body model, which includes: obtaining a customized human body model customized for a user by modeling; comparing standard figure information of a body part with figure information of the same body part in the customized human body model of the user to determine whether the body part of the user has an abnormal figure;
  displaying information about the abnormal figure of the body part of the user, in response to a presence of an abnormal figure.
  In an embodiment, the customized human body model of the user has multiple customized body surface feature points marked on a human body surface and multiple customized bone points marked on a human skeleton.
  Comparing the standard figure information of the body part with the figure information of the same body part in the customized human body model of the user to determine whether t the body part of the user has an abnormal figure, includes:
  Comparing at least one of a waistline, a hipline, a chest circumference, and a bending angle of the multiple customized bone points of the customized human body model of the user with a corresponding one of a threshold range of a standard waistline, a threshold range of a standard hipline, a threshold range of a standard chest circumference, and a standard bending angle of skeleton, to obtain a comparison result;
  Determining whether the body part of the user has an abnormal figure according to the comparison result.

In an embodiment, the comparing the standard figure information of the body part with the figure information of the same body part in the customized human body model of the user to determine whether the body part of the user has an abnormal figure, includes:
  Providing a reference human body model which has multiple reference body surface feature points marked on a human body surface and multiple reference bone points marked on a human skeleton;
  Comparing at least one of a waistline, a hipline, a chest circumference, and positional relationships between customized bone points of the customized human body model of the user with a corresponding one of a waistline, a hipline, a chest circumference, and positional relationships between reference bone points of the reference human body model, to obtain a comparison result, wherein the waistline, the hipline, and the chest circumference of the reference human body model indicate a threshold range of a standard waist circumstance, a threshold range of a standard hip circumstance, and a threshold range of a standard chest circumstance of a human body, respectively, and the positional relationship between the reference bone points of the reference human body model indicates a standard skeleton structure of the human body;
  Determining whether the body part of the user has an abnormal figure according to the comparison result.
  In an embodiment, the abnormal figure of the body part includes at least one of obesity, shortness, forward head, head tilt, kyphosis, uneven shoulders, scoliosis, pelvic tilt, knee hyperextension, O-shaped legs, and X-shaped legs.
  In an embodiment, after the displaying information about the abnormal figure of the body part of the user, the method further includes: displaying health advice information corresponding to the abnormal figure according to the abnormal figure of the body part of the user.
  In an embodiment, obtaining the customized human body model customized for the user by modeling includes:
  Acquiring a human body size of the user;
  Performing a scaling process on a standard human body model according to the human body size, to obtain a reference human body model matching the human body size of the user, the reference three-dimensional human body model having multiple reference body surface feature points marked on a human body surface and multiple reference bone points marked on a human skeleton, and the multiple reference body surface feature points and the multiple reference bone points being divided into multiple sets of reference control points, each set of reference control points including two of the reference body surface feature points and one of the reference bone points that are arranged in a width direction of a body part;
  Acquiring a human body image of the user;
  Obtaining sizes of body parts of the user according to the human body image;
  Determining to-be-moved target positions of each reference body surface feature point and the reference bone point of each set of reference control points of the reference human body model, according to the sizes of the body parts of the user;
  Adjusting each reference body surface feature point and each reference bone point of the reference human body model to the to-be-moved target positions to obtain the customized human body model of the user.
  In an embodiment, the human body size of the user is a height value of the user.

Performing a scaling process on the standard human body model according to the human body size to obtain the reference human body model matching the human body size of the user, includes:
  Determine a height scaling ratio according to the height value of the user and a height value of the standard human body model;
  Performing a scaling process on the standard human body model in a vertical direction according to the height scaling ratio, to obtain the reference human body model having a height value is equal to the height value of the user.

In an embodiment, the height scaling ratio is a quotient obtained by dividing the height value of the user by the height value of the standard human body model.

In an embodiment, the standard human body model has multiple standard body surface feature points marked on a human body surface and multiple standard bone points marked on a human skeleton, the multiple standard body surface feature points and the multiple standard bone points are divided into multiple sets of standard control points, each set of standard control points includes two of the standard body surface feature points and one of the standard bone points that are arranged in a width direction of a body part.

Performing a scaling process on the standard human body model in the vertical direction according to the height scaling ratio to obtain the reference human body model having a height value equal to the height value of the user, includes: performing a scaling process on a distance between any adjacent standard control points in the vertical direction of the standard human body model according to the height scaling ratio to obtain the reference human body model, with the standard body surface feature points serving as the reference body surface feature points, and the standard bone points serving as the reference bone points.

In an embodiment, the determining to-be-moved target positions of each reference body surface feature point and the reference bone point of each set of reference control points of the reference human body model according to the sizes of the body parts of the user, includes:
  Dividing a length of a body part of the user by a first distance between two adjacent reference body surface feature points in the reference three-dimensional human body mode, the first distance characterizing the length of the same body part, to obtain a length scaling ratio of the two adjacent reference body surface feature points characterizing the length of the body part;
  Recognizing multiple body surface feature points in the human body image by using image recognition, wherein a midpoint of a line connecting two adjacent body surface feature points in a horizontal direction is used as a bone point of the human body image, the two adjacent body surface feature points representing a body part, and
  Determining, in the human body image of the user, a distance in the horizontal direction between two immediately adjacent bone points in a length direction of a same body part of the user;
  Dividing the distance in the horizontal direction by a length of the body part in the human body image of the user, to obtain a sine value representing deformation of the body part;
  Keeping unchanged a position of one reference bone point of the reference human body model corresponding to one bone point of the two immediately adjacent bone points of the human body image, and determining a to-be-moved target position of another reference bone point of the reference human body model corresponding to the other bone point of the two immediately adjacent bone points of the human body image according to the sine value and the length scaling ratio, wherein the multiple body surface feature points of the human body image are in one-to-one correspondence with the multiple reference body surface feature points of the reference human body model one-to-one, and the multiple bone points of the human body image are in one-to-one correspondence with the multiple reference bone points of the reference human body model.

In an embodiment, determining to-be-moved target positions of each reference body surface feature point and the reference bone point of each set of reference control points of the reference human body model according to the sizes of the body parts of the user, includes:
  Dividing a width of a body part of the user by a second distance between two adjacent reference body surface feature points of the reference human body model the second distance characterizing the width of the same body part, to obtain a width scaling ratio of the two adjacent reference body surface feature points characterizing the width of the body part;
  Keeping unchanged the to-be-moved target position of the reference bone point, and determining to-be-moved target positions, in the width direction of the body part, of two reference body surface feature points symmetrically distributed on either side of the reference bone point according to the width scaling ratio.

In an embodiment, obtaining the sizes of the body parts of the user according to the human body image includes:
  Recognizing multiple body surface feature points in the human body image by using image recognition;
  Calculating a spatial distance in three-dimensional coordinate system of two adjacent body surface feature points characterizing a size of a body part of the user among the multiple body surface feature points, as the size of the body part of the user.

In an embodiment, calculating the spatial distance in the three-dimensional coordinate system of two adjacent body surface feature points characterizing a size of a body part of the user among the multiple body surface feature points as the size of the body part of the user, includes:
  Establishing a plane coordinate system in the human body image of the user;
  Determining a position of each of the body surface feature points of the human body image in the plane coordinate system;
  Converting the position of each of the body surface feature points in the plane coordinate system into a position of each of the body surface feature points in the three-dimensional coordinate system according to a height of the user; and
  Calculating the spatial distance between the two adjacent body surface feature points in the three-dimensional coordinate system according to the position of each of the body surface feature points in the three-dimensional coordinate system.

In an embodiment, before performing the scaling process on the standard human body model according to the human body size, the method further includes:
  Acquiring, in a database, a standard human body model matching category information of the user according to the category information of the user, the category information of the user including at least one of gender, race, and age.

In an embodiment, the modeling method further includes: displaying at least one of the standard human body model, the human body image, the reference human body model, and the human body model of the user.

In another aspect, provided is a modeling device for a human body model, which includes:

A modeling component configured to obtain a customized human body model customized for a user by modeling;

An abnormal figure determination component configured to compare standard figure information of a body part with figure information of the same body part in the customized human body model of the user to determine whether the body part of the user has an abnormal figure;

A display unit configured to display information about the abnormal figure of the body part of the user, in response to a presence of an abnormal figure.

In still another aspect, provided is an electronic device which includes: a processor; and a storage configured to store machine-readable instructions which, when executed by the processor, cause the processor to execute the above modeling method for a human body model.

In an embodiment, a display unit is electrically connected to the processor, and is configured to display at least one of a standard human body model, a human body image, a reference human body model, and a human body model of a user.

In further still another aspect, provided is a computer-readable storage medium with a computer program stored thereon, when executed by a processor, the computer program implementing the above modeling method for a human body model.

DETAIL DESCRIPTION OF EMBODIMENTS

In order to enable those skilled in the art to better understand the technical solutions of the present disclosure, the present disclosure will be further described in detail below with reference to the accompanying drawings and specific implementations.

Figure 1:
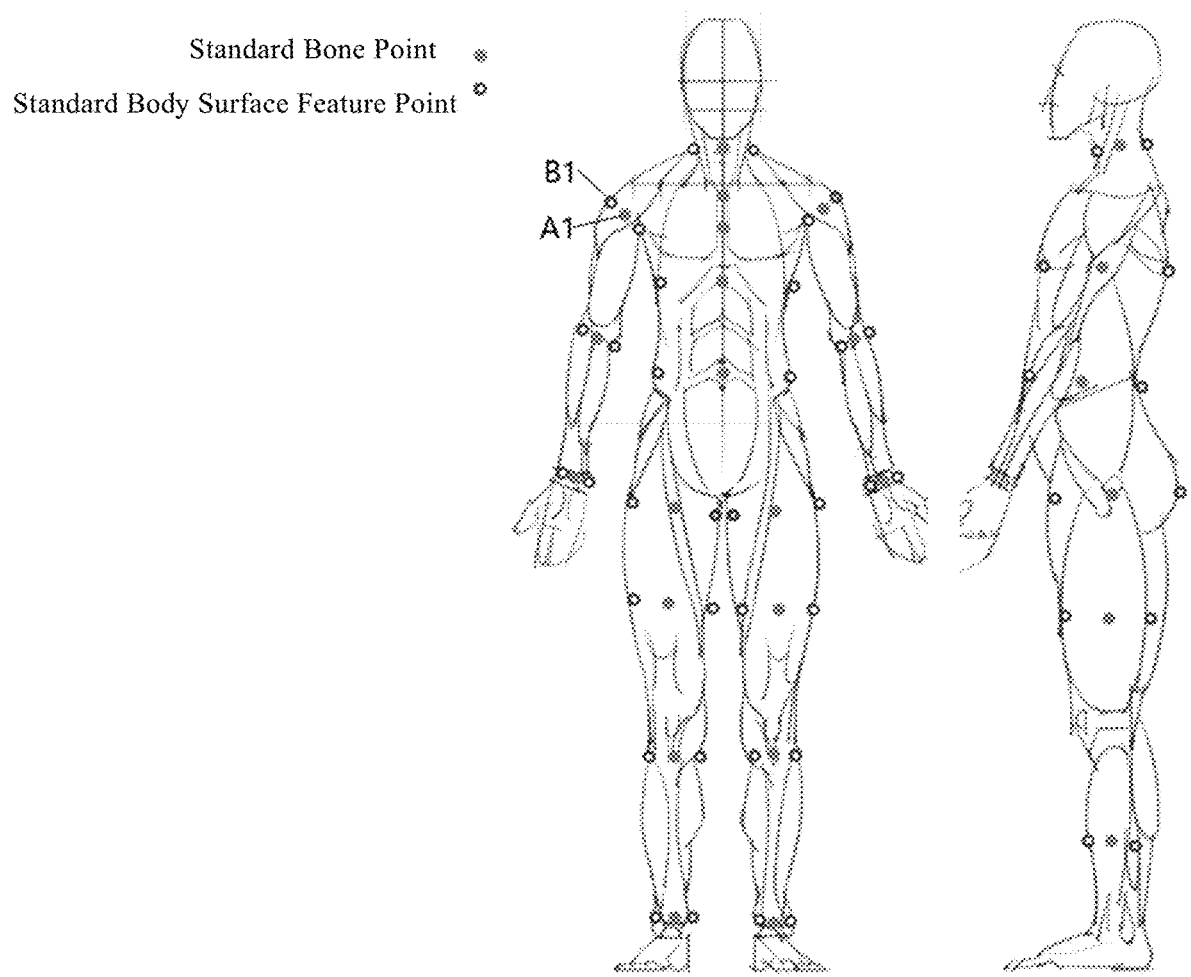
FIG. 1 is a schematic diagram of a standard three-dimensional human body model according to an embodiment of the present disclosure.

As shown in FIG. 1, a standard three-dimensional human body model is a digital human body model. The standard three-dimensional human body model includes bone points marked on the skeleton and body surface feature points marked on the human body surface. Bone points are generally marked on the key axis parts when human body moves, for example, nodes at the end of a human bone, such as joints, and body surface feature points may be marked on the human body surface near the bone points to characterize body parts. By changing the positions of the bone points and the body surface feature points in the standard three-dimensional human body model, the body shape (such as tall, short, fat and thin), figure and action of the standard three-dimensional human body model can be changed.

Similarly, the modeling method of the present application can also be used to model a two-dimensional human body model of a user based on a standard two-dimensional human body model. The standard two-dimensional human body model includes bone points marked on the skeleton and body surface feature points marked on the human body surface. Bone points are generally marked on key axis parts when human moves, for example, nodes at the end of a human bone, such as joints. Body surface feature points may be marked on the human body surface near the bone points to characterize body parts. By changing the positions of the bone points and the body surface feature points in the standard two-dimensional human body model, the body shape (such as tall, short, fat and thin), figure and action of the standard two-dimensional human body model can be changed.

The present disclosure will be describe in detail by taking a three-dimensional human body model as an example. However, those skilled in the art should know that this application is also applicable to the modeling of a two-dimensional human body model.

Both the reference three-dimensional human body model and the customized three-dimensional human body model below are obtained by changing the positions of the bone points and body surface feature points in the standard three-dimensional human body model. In order to facilitate the distinction, the bone points and body surface feature points of the standard three-dimensional human body model are marked as standard bone points A1 and standard body surface feature points B1, respectively; the bone points and body surface feature points of the reference three-dimensional human body model are marked as reference bone points A2 and reference body surface feature points B2, respectively; the bone points and body surface feature points of the customized three-dimensional human body model are marked as customized bone points A4 and customized body surface feature points B4, respectively.

The standard bone points A1 of the standard three-dimensional human body model, the reference bone points A2 of the reference three-dimensional human body model, and the customized bone points A4 of the customized three-dimensional human body model are in one-to-one correspondence to each other, respectively. The standard body surface feature points B1 of the standard three-dimensional human body model, the reference body surface feature points B2 of the reference three-dimensional human body model, and the customized body surface feature points B4 of the customized three-dimensional human body model are in one-to-one correspondence to each other, respectively.

The standard three-dimensional human body model has multiple standard body surface feature points B1 marked on the human body surface and multiple standard bone points A1 marked on the human skeleton, and the multiple standard bone points A1 and the multiple standard body surface feature points B1 are divided into multiple sets of standard control points, and each set of standard control points includes two of the standard body surface feature points B1 and one of the standard bone points A1 arranged in a width direction of a body part.

The reference three-dimensional human body model has multiple reference body surface feature points B2 marked on the human body surface and multiple reference bone points A2 marked on the human skeleton, and the multiple reference body surface feature points B2 and the multiple reference bone points A2 are divided into multiple sets of reference control points, each set of reference control points includes two of the reference body surface feature points B2 and one of the reference bone points A2 arranged in a width direction of a body part.

The body surface feature points B3 in the human body image of the user are various position points on the human body surface recognized from the real image of the user's body, and are used to characterize body parts.

In the human body image, only the body surface feature point B3 can be recognized, but not the bone points.

Among the multiple body surface feature points B3 in the human body image, two adjacent body surface feature points in the length direction of a body part may characterize a length of the body part; among the multiple body surface feature points B3 in the human body image, two adjacent body surface feature points in the width direction of a body part may characterize a width of the body part.

For example, in a human body image, two adjacent body surface feature points in the length direction of a shank may characterize a length of the shank. In the human body image, two adjacent body surface feature points in the width direction of the shank may characterize a width of the shank.

An electronic device 500 provided in the present disclosure is an execution subject of a modeling method of a three-dimensional human body model. The technical solutions of the present disclosure will be describe in detail by taking the electronic device 500 as the execution subject as an example.

Figure 2:
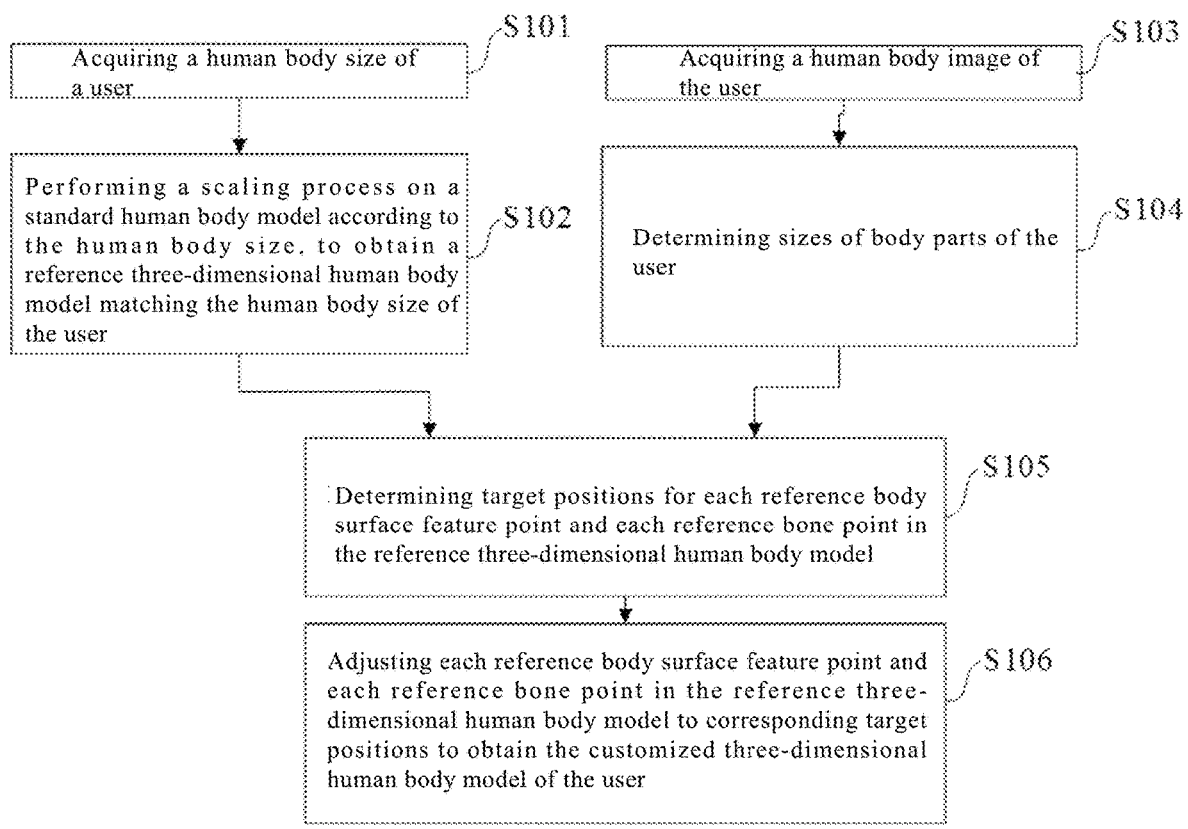
FIG. 2 is a schematic flowchart of a modeling method for a three-dimensional human body model according to an embodiment of the present disclosure.

An embodiment of the present disclosure provides a modeling method of a three-dimensional human body model. As shown in FIG. 2, the modeling method includes steps S101 to S106.

At step S101: a human body size of a user is acquired.

The human body size of the user may characterize the body shape characteristic of the user's real body (such as tall, short, fat, thin, etc.). The human body size may include a height value, a length value of the arm, a length value of the leg, a width value of the shoulder, a chest circumference, a waistline, and a hipline, etc., of the user.

In an embodiment of the present disclosure, step S101 includes: acquiring the height value of the user as the human body size.

At step S102: a scaling process is performed on a standard human body model according to the human body size, to obtain a reference three-dimensional human body model matching the human body size of the user, and then step S105 is performed.

At step S102, performing the scaling process on the standard three-dimensional human body model may include adjusting positions of the bone points and positions of the body surface feature points of the standard three-dimensional human body model, thereby changing the body shape of the standard three-dimensional human body model to obtain a reference three-dimensional human body model.

At steps S101 and S102, based on the standard three-dimensional human body model, the standard three-dimensional human body model is automatically scaled according to the human body size of the user, to generate a reference three-dimensional human body model that is more similar to the user's body shape.

Therefore, the positions of the standard body surface feature points and the bone points of the standard three-dimensional human body model can match desired target positions thereof, which reduces the amount of calculation during subsequent steps and helps to improve the process speed.

In an embodiment of the present disclosure, when the human body size of the user is the height value, step S102 includes: determining a height scaling ratio according to the height value and the height value of the standard three-dimensional human body model; and scaling the standard three-dimensional human body model according to the height scaling ratio, to obtain a reference three-dimensional human body model matching the body height feature of the user.

At step S103: a human body image of the user is acquired.

At step S103, the human body image of the user is a two-dimensional image, and may include at least one of a front image, a side image, and a back image of the user, and may also include images from other angles of the user. In one embodiment, the human body image of the user may include a local image of the user, such as at least one of a local front image, a local side image, and a local back image, such as an image of the head, an image of the back, an image of the shoulders, an image of the spine, an image of the pelvis, an image of the leg, an image of the knee, etc.

At step S104: an actual size of a body part of the user is obtained according to the human body image.

In an embodiment of the present disclosure, step S104 includes: recognizing multiple body surface feature points B3 in the human body image by using a recognition model; calculating a spatial distance of each pair of associated body surface feature points B3 in the three-dimensional coordinate system, as the actual size of the body part of the user.

It should be noted that each body surface feature point B3 is associated with at least one body surface feature point B3. Two adjacent body surface feature points B3 may form a pair of associated body surface feature points B3, and characterize the actual size of the body part of the user.

Figure 5:
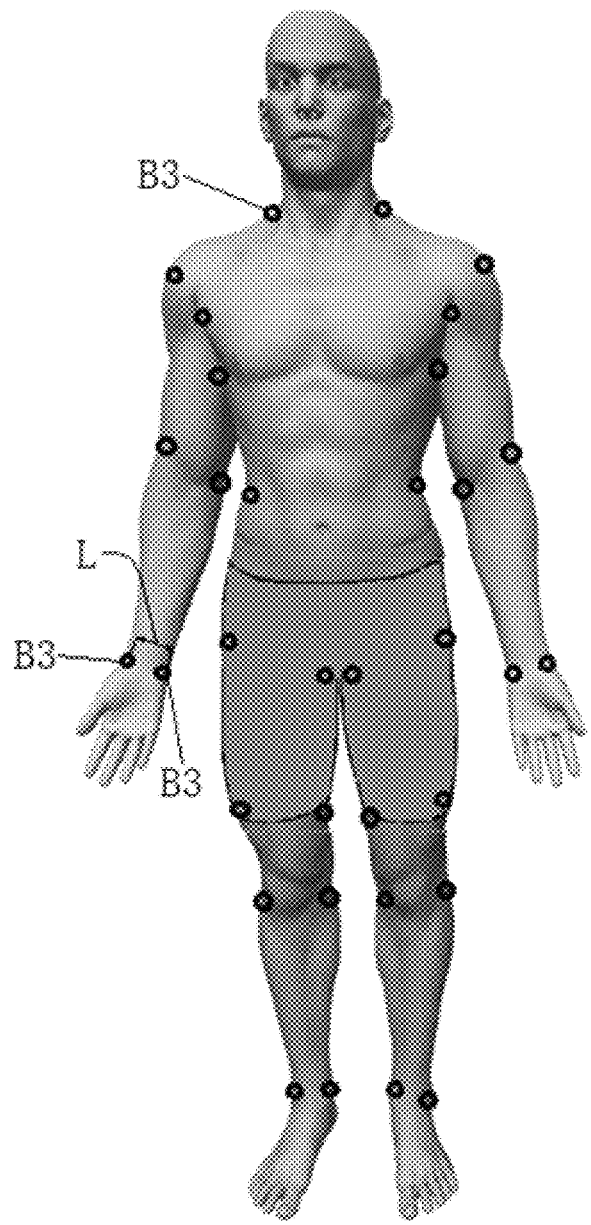
FIG. 5 is a schematic diagram of the distribution of body surface feature points of a human body image of a user, according to an embodiment of the present disclosure.

In the front image of the human body shown in FIG. 5, the two body surface feature points B3 at the right wrist may form a pair of associated body surface feature points B3 and characterize a width of the right wrist of the user.

The scaling process includes adjusting the positions of bone points and body surface feature points in the standard three-dimensional human body model to zoom in or out the distance between a pair of associated body surface feature points B3 for characterize the right wrist of the user (i.e., the width of the right wrist).

In the three-dimensional coordinate system, the spatial distance L between the two individual feature points B3 serves as the actual size of the user's body part.

At step S105: a target position to which each reference body surface feature point B2 in the reference three-dimensional human body model will be adjusted and a target position to which each reference bone point A2 will be moved are determined, according to the size of the user's body part.

At step S105, the positions of the reference body surface feature points B2 and the reference bone points A2 in the reference three-dimensional human body model are actually further corrected, adjusted or moved according to the positions of the body surface feature points B3 in the user's human body image, to obtain the target positions to which the reference body surface feature points B2 will be adjusted and the target positions to which the reference bone points A2 will be moved.

In an embodiment of the present disclosure, step S105 includes:
  determining a local scaling ratio of each pair of associated reference body surface feature points B2, according to the size of the user's body part and the distance between the pair of associated reference body surface feature points B2 characterizing the size of the same body part;
  determining a target position to which each reference body surface feature point B2 will be adjusted, according to the local scaling ratio of each pair of associated reference body surface feature points B2;
  determining a target position to which each reference bone point A2 will be adjusted, according to the target position of each reference body surface feature point B2 and a positional relationship between the reference bone point A2 and the reference body surface feature point B2.

At step S106: each reference body surface feature point and each reference bone point in the reference three-dimensional human body model are adjusted to corresponding target positions to obtain a customized three-dimensional human body model of the user.

At steps S103 to S106, position information of the feature points of the human body image of the user is automatically recognized firstly, and then the reference three-dimensional human body model is adjusted more precisely according to the position information of the feature points of the human body image of the user, so that the reference three-dimensional human body model can be further closer to the real body shape characteristic of the user, and finally a customized three-dimensional human body model that matches the user's real body shape can be generated, which improves the reality of the customized three-dimensional human body model.

In an embodiment of the present disclosure, before step S102, the method further includes: acquiring, in a three-dimensional human body model library, a standard three-dimensional human body model matching category information of the user, according to the category information of the user, the category information of the user including at least one of gender, race, and age.

Optionally, the modeling method for a three-dimensional human body model provided by an embodiment of the present disclosure further includes: controlling a display unit 503 to display at least one of a standard three-dimensional human body model, a human body image, a reference three-dimensional human body model, and a customized three-dimensional human body model.

Optionally, after obtaining the customized three-dimensional human body model of the user, the method further includes: determining whether the body part of the user has an abnormal figure according to standard figure information (i.e., reference figure information) of the body part and the customized three-dimensional human body model of the user; and if the body part of the user has an abnormal figure, displaying abnormal figure information about the body part of the user.

In the embodiments of the present disclosure, during the process of performing the modeling method for a human body model of the present disclosure, the standard three-dimensional human body model is firstly used as the basis, and the standard three-dimensional human body model is automatically roughly scaled according to the human body size of the user, to generate a reference three-dimensional human body model more similar to the body shape of the user. Therefore, the positions of the feature points and bone points of the standard three-dimensional human body model can match their desired target positions, which reduces the amount of calculation in subsequent steps and helps to improve the process speed.

After that, the position information of the feature points of the human body image of the user is automatically recognized; and then the reference three-dimensional human body model is adjusted or scaled precisely according to the position information of the feature points of the human body image of the user, so that the reference three-dimensional human body model is further closer to the real body shape characteristic of the user, and finally a customized three-dimensional human body model that matches the user's real body shape can be generated.

The above modeling method for a three-dimensional human body model can be executed by the electronic device itself. Compared with the manual modeling method, the modeling method of the present disclosure is faster and more efficient, and the generated three-dimensional human body model has a higher matching degree with the user's body shape.

Figure 3:
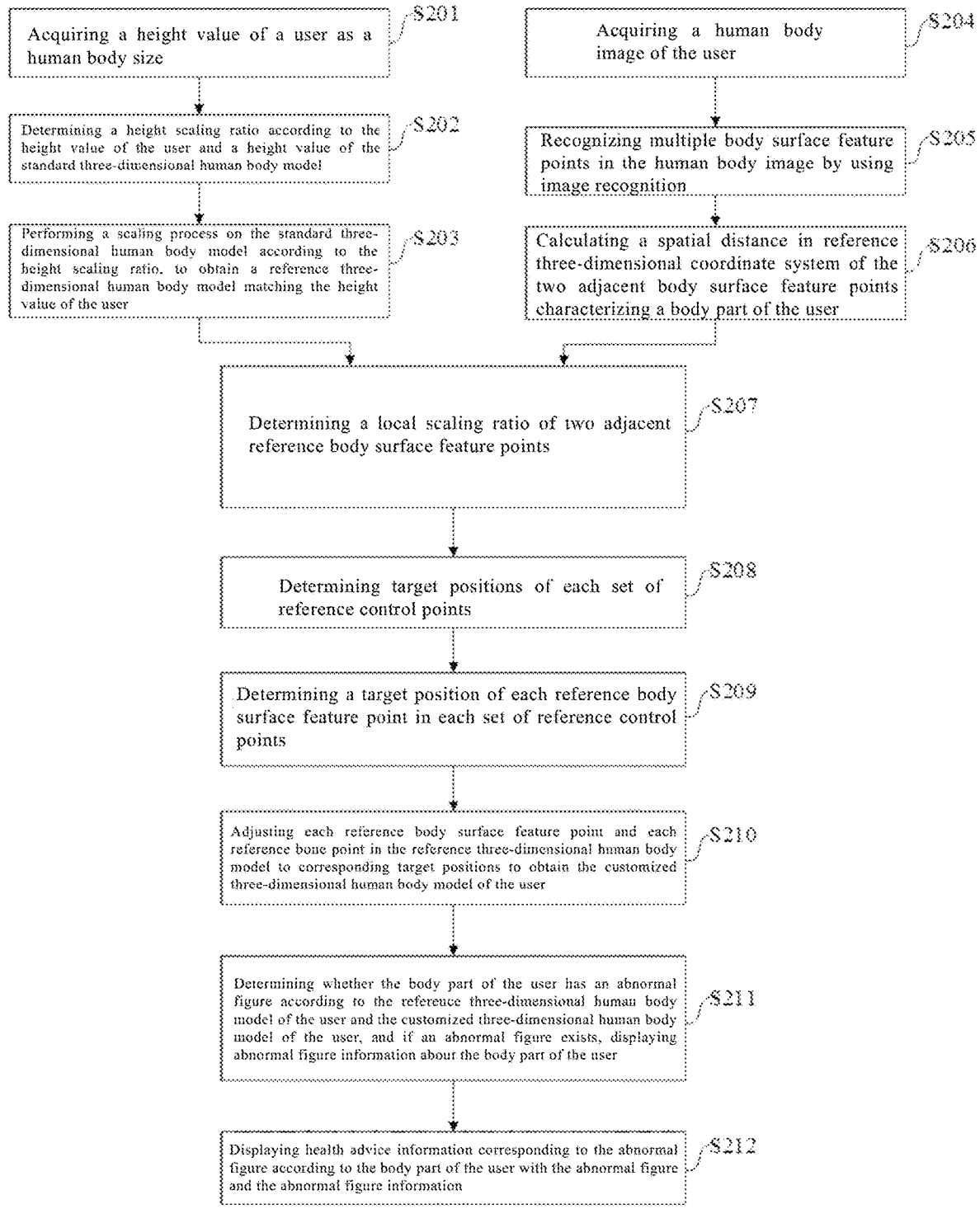
FIG. 3 is a schematic flowchart of a modeling method for a three-dimensional human body model according to an embodiment of the present disclosure.

An embodiment of the present disclosure also provides another modeling method for a three-dimensional human body model. As shown in FIG. 3, the modeling method includes steps S201 to S212.

At step S201: a height value of a user is acquired as a human body size.

It should be noted that, the human body size of the user may characterize the body shape characteristic of the user's real body (such as tall, short, fat, thin, etc.). The human body size may include a height value, a length value of the arm, a length value of the leg, a width value of the shoulders, a chest circumference, a waistline, and a hipline, etc., of the user.

Since the height value is a relatively intuitive and evident body shape characteristic, the height value is selected as the user's body size, thereby ensuring that the reference three-dimensional human body model obtained in the subsequent steps is very close to the user's body shape characteristic.

Optionally, the electronic device 500 has an information input unit, and the user's body size (for example, a height value) is input through the input unit, so that the electronic device 500 may obtain the user's body size. The input mode supported by the information input unit of the electronic device 500 may be determined according to actual design requirements, such as touch input or voice input, etc. The specific type of the information input unit will be further introduced in the subsequent content.

Optionally, the electronic device 500 may communicate with another device (such as another electronic device 500 or a server), and the other device stores the user's body size (such as a height value). The electronic device 500 sends a request to the other device, and the other device sends the user's body size to the electronic device 500 according to the request, so that the electronic device 500 can obtain the user's body size.

In an embodiment of the present disclosure, before step S201, the method further includes: acquiring, in a three-dimensional human body model library, a standard three-dimensional human body model matching category information of the user according to the category information of the user, the category information of the user including at least one of gender, race, and age.

The inventor of the present disclosure found that users with different category information (e.g., the gender, race, and age) have large differences in body shape characteristic. Therefore, a variety of standard three-dimensional human models may be stored in a database such as a three-dimensional human model library. Users are divided into different user groups according to category information, and each user group corresponds to a standard three-dimensional human body model. Therefore, a standard three-dimensional human body model, which more closely matches the user's body shape characteristic, can be obtained according to the user's category information, which helps to reduce the amount of calculation in subsequent steps. For example, a male standard three-dimensional human body model can be selected for a male user, and a female standard three-dimensional human body model can be selected for a female user. A standard three-dimensional human body model for children is selected for a child; and a standard three-dimensional human body model for elderly is selected for an elderly person.

At step S202: a height scaling ratio is determined according to the height value of the user and a defined height value of the standard three-dimensional human body model.

In an embodiment of the present disclosure, assuming that the user's height value is 1.6 meters, and the defined height value of the standard three-dimensional human body model is 1.8 meters. By dividing the user's height value by the defined height value of the standard three-dimensional human body model, a quotient obtained is approximately equal to 0.89, therefore 0.89 can be used as the height scaling ratio. Of course, other calculation methods can also be used to perform calculation on both of the height value of the user and the defined height value of the standard three-dimensional human body model to obtain the height scaling ratio.

Optionally, in step S201 and/or step S202, the display unit 503 of the electronic device 500 may display the standard three-dimensional human body model.

At step S203: a scaling process is performed on the standard three-dimensional human body model according to the height scaling ratio, to obtain a reference three-dimensional human body model matching the body height feature of the user, and then step S207 is performed.

Figure 4:
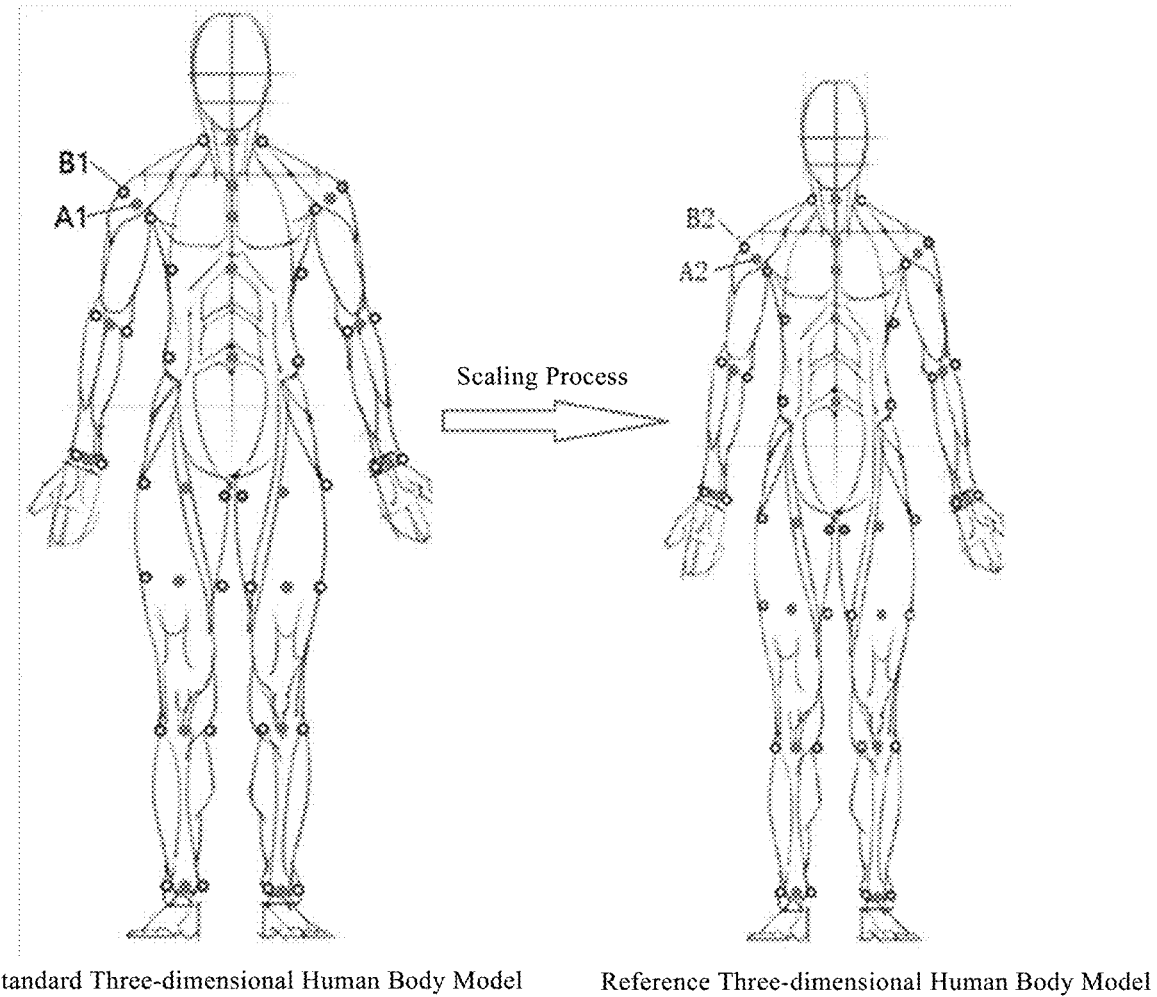
FIG. 4 is a schematic diagram of converting a standard three-dimensional human body model into a reference three-dimensional human body model, according to an embodiment of the present disclosure.

As shown in FIG. 4, performing a scaling process on the standard three-dimensional human body model includes: adjusting a position of each body surface feature point in the standard three-dimensional human body model, to change the body shape of the standard three-dimensional human body model, thereby obtaining a reference three-dimensional human body model. When the user's height value is used as a human body size, the height value of the reference three-dimensional human body model should be equal to the user's height value.

In an embodiment of the present disclosure, step S203 includes steps a1 and a2.

At step a1, a scaling process is performed on a distance between the standard body surface feature points B1 that are immediately adjacent in the vertical direction (i.e., the height direction) in the standard three-dimensional human body model and a distance between the standard bone points A1 that are immediately adjacent in the vertical direction, according to the height scaling ratio.

At step a2, the scaled standard three-dimensional human body model serves as a reference three-dimensional human body model, wherein the standard body surface feature points B1 in the standard three-dimensional human body model are used as reference body surface feature points B2 of the reference three-dimensional human body model, and the standard bone points A1 in the standard three-dimensional human body model are used as reference bone points A2 of the reference three-dimensional human body model.

In the process of performing steps S201 and S203, the standard three-dimensional human body model is firstly used as the basis, and the standard three-dimensional human body model is automatically scaled according to the height value of the user, to generate a reference three-dimensional human body model more similar to the body shape of the user. Since the height value is a relatively intuitive and evident body shape characteristic, just selecting the height value as the user's body size can also ensure that the reference three-dimensional human body model obtained in the subsequent steps is very close to the user's body shape characteristic, reducing the types and quantities of the human body sizes that need to be acquired. In addition, the positions of the reference body surface feature points and the positions of reference bone points of the reference three-dimensional human body model are further closer to the desired target position, which reduces the amount of calculation in subsequent steps, and helps to improve the process speed.

Optionally, in step S203, the display unit 503 of the electronic device 500 may display the standard three-dimensional human body model and the reference three-dimensional human body model.

At step S204: a human body image of the user is acquired.

In an embodiment of the present disclosure, the electronic device 500 acquires a front image, a side image and a back image of the human body of the user. In an embodiment, the electronic device 500 acquires a full-body image of the user.

Optionally, the electronic device 500 has a camera function, and when step S204 is performed, the electronic device 500 turns on a camera to take photo of the user, and acquires the human body image of the user.

Optionally, the human body image of the user is stored in the electronic device 500 in advance, and when step S103 is performed, the electronic device 500 directly calls the human body image of the user.

Optionally, the electronic device 500 may communicate with other devices (such as another electronic device 500 or a server). The other device stores the human body image of the user. The electronic device 500 sends a request to the other device, and the other device sends the stored image of human body of the user to the electronic device 500 according to the request, so that the electronic device 500 acquires the human body image of the user.

Optionally, in the process of step S204, the display unit 503 of the electronic device 500 may display the human body image of the user, or may simultaneously display the reference three-dimensional human body model.

At step S205: multiple body surface feature points in the human body image by using a recognition model are recognized.

As shown in FIG. 5, multiple body surface feature points B3 in the human body image may be represented by circles in the figure. Each of the multiple body surface feature points B3 is located on the human body surface, and is located at a body part of the human body and used to characterize the body part. Each pair of associated body surface feature points B3 are used to characterize the shape of the body part. For example, a pair of body surface feature points B3 immediately adjacent in the lateral direction located at the neck may characterize a width of the neck. A pair of body surface feature points B3 immediately adjacent in the lateral direction located at the left wrist may characterize a width of the left wrist. A body surface feature point B3 located at the knee joint and a body surface feature B3 located at the ankle joint may characterize a length of the shank, and so on.

The recognition model has an image recognition function, which can process, analyze and understand images to recognize targets and objects in various different modes.

Recognition models in this field can be obtained by training through machine learning. The training process may generally include: preparing a large number of (such as 100,000) human body images in advance, manually marking the body surface feature points B3 of each human body image, and training a neural network by recognizing the large number of body surface feature points B3 of the human body images. The specific training process will not be repeated here.

At step S206: a spatial distance in the three-dimensional coordinate system of each pair of associated body surface feature points B3 in the three-dimensional coordinate system is calculated, and the spatial distance serves as the size of a body part of the user.

In the embodiments of the present disclosure, the three-dimensional coordinate system can be defined according to actual needs; the world coordinate system or the local coordinate system can also be used as the three-dimensional coordinate system. In fact, the distance of each pair of associated body surface feature points B3 in the three-dimensional coordinate system (which is a straight line distance) is the actual distance of each pair of associated body surface feature points B3 on the user's real body.

At step S207: a scaling ratio (i.e., a length scaling ratio) of a pair of associated adjacent reference body surface feature points B2 in a length direction of a body part is determined, according to the length of the body part of the user and a first distance between the pair of associated adjacent reference body surface feature points B2 corresponding to each pair of associated adjacent body surface feature points B3.

Take two adjacent body surface feature points B3 at the thighs of the human body image of the user as an example. A pair of associated (i.e., adjacent) body surface feature points B3 at the thighs of the human body image of the user correspond to a pair of associated reference body surface feature points B2 at the thighs of the reference three-dimensional human body model.

Assuming that the length of the user's thigh is 0.35 m (L1=0.35 m), the defined distance (i.e., the first distance) between two adjacent reference body surface feature points B2 used to characterize the thigh of the reference three-dimensional human body model is 0.4 meters. After dividing the length of the thigh (L1=0.35 meters) by the first distance of 0.4 meters, the quotient obtained is approximately equal to 0.875, therefore 0.875 may be used as the length scaling ratio.

At step S208: as for each set of reference control points including a reference bone point A2 and two reference body surface feature points B2 as a unit, target positions to which each reference body surface feature point B2 and the reference bone point A2 in each set of reference control points will be moved in the length direction of the body part is determined, according to the length scaling ratio.

It should be noted that the standard three-dimensional human body model and the reference three-dimensional human body model are both constructed in the same three-dimensional coordinate system. In the reference three-dimensional human body model, the coordinates of the reference body surface feature points B2 and the coordinates of the reference bone points in the three-dimensional coordinate system are known, and the positions of the reference body surface feature points B2 and the positions of the reference bone points can be represented by coordinates.

The positional relationship between the bone points of the human body image can reflect the deformation of a body part of the user.

In order to reflect the deformation of a body part of the human body, when determining the target positions to which each of the reference body surface feature point B2 and the reference bone point A2 of each set of reference control points will be moved in the length direction of the body part, step S208 further includes: recognizing multiple body surface feature points in the human body image by using image recognition. According to the positional relationship between the body surface feature points and the bone point, the position of the bone point in the human body image can be determined, in other words, in the human body image, a midpoint of the line connecting two adjacent body surface feature points in the horizontal direction is the bone point.

Figure 13:
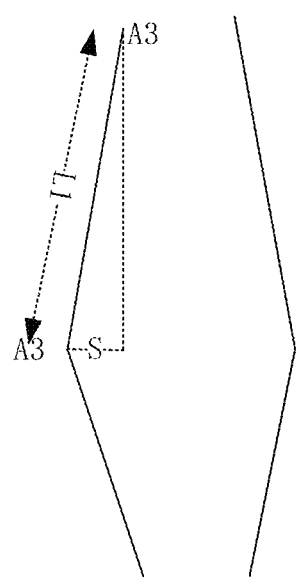
FIG. 13 is a schematic diagram of O-shaped legs in a human body diagram of a user according to an embodiment of the present disclosure.

FIG. 13 is a schematic diagram of O-shaped legs in a human body diagram of a user according to an embodiment of the present disclosure. When a body part of a user is deformed, such as knee hyperextension, O-legs, etc., a distance S in the horizontal direction of two bone points A3 immediately adjacent to each other in the length direction of a user's body part (for example, thigh) in the human body image of the user is determined.

The distance S in the horizontal direction is divided by the length of the user's body part (for example, a length of the thigh) in the human body image of the user, to obtain the sine value $\sin \theta = S/L$ that represents the deformation of this body part.

The position of the reference bone point (this reference bone point corresponds to a bone point of the two adjacent bone points A3 at the root of the thigh in the human body image) at the root of the thigh in the reference human body model is kept unchanged. According to the sine value and the length scaling ratio, the target position to which the bone point located at the knee part in the reference human body model (that is, the other reference bone point in the reference human body model that corresponds to the other bone point of the two immediately adjacent bone points) will be moved is determined. The sine value may determine the direction along which the reference bone point will be moved, and the length scaling ratio may determine the position to which the reference bone point will be moved in the length direction of the body part.

The multiple body surface feature points of the human body image are in one-to-one correspondence with the multiple reference body surface feature points of the reference human body model, and the multiple bone points of the human body image are in one-to-one correspondence with the multiple reference bone points of the reference human body model.

Continuing the above example, new coordinates of the two adjacent reference bone points A2 on the thigh are determined, so that the distance between the pair of reference bone points A2 with the new coordinates is shortened to 0.875 times the original distance, and the line connecting the pair of reference bone points A2 with the new coordinates forms an angle θ with the vertical direction.

After the bone points are moved according to the sine value sin θ=S/L, the reference human body model can reflect the deformation of the user's leg bones.

This method is also suitable for determining the deformation of bones in other body parts, such as forward head, head tilt, kyphosis, uneven shoulders, scoliosis, pelvic tilt, knee hyperextension, O-shaped legs, and X-shaped legs.

At step S209: as for each set of reference control points, a target position to which each reference body surface feature point B2 in the set of reference control points will be moved in the width direction of the body part is determined, according to a target position of the reference bone point and a positional relationship between the reference bone point A2 and the reference body surface feature point B2.

A reference body surface feature point B2 is arranged near each reference bone point A2. In the three-dimensional coordinate system, the coordinates of the reference bone points A2 and the coordinates of the reference body surface feature points B2 can be converted through a preset conversion relationship.

According to the new coordinates of the reference body surface feature points B2 in the three-dimensional coordinate system determined according to the above steps, new coordinates of the reference bone point A2 in the three-dimensional coordinate system are determined. The positions represented by the new coordinates of the reference body surface feature points B2 in the three-dimensional coordinate system serve as the target positions of the reference body surface feature points B2.

In an embodiment of the present disclosure, step S209 includes: keeping the target position of each reference bone point A2 unchanged, and determining the target positions to which the two reference body surface feature points B2 on either side of each reference bone point A2 will be moved in the direction (i.e., the width direction of the body part) of the line connecting the two reference body surface feature points B2, according to the width scaling ratio.

At least two reference body surface feature points B2 are arranged near each reference bone point A2, and the two reference body surface feature points B2 are symmetrically distributed on both sides of the reference bone point A2.

As for a reference bone point A2, the coordinates of the reference bone point A2 is kept unchanged, and new coordinates in the three-dimensional coordinate system of two reference body surface feature points B2 symmetrically distributed on both sides of the reference bone point A2 are determined as target positions of the two reference body surface feature point B2.

Assuming that the width of the user's right wrist is 0.05 meters (L=0.05 meters), a defined distance (i.e., a second distance) between two corresponding reference body surface feature points B2 characterizing the width of the right wrist of the reference three-dimensional human body model is 0.06 meters. After dividing the width of the right wrist (L=0.05 meters) by the defined distance, the quotient obtained is approximately equal to 0.83, therefore 0.83 may be used as the width scaling ratio.

The determining the target positions of two adjacent reference body surface feature points B2 for characterizing the width of the right wrist of the reference three-dimensional human body model includes: determining new coordinates of the two adjacent reference body surface feature points B2 so that a distance between a pair of reference body surface feature points B2 with the new coordinates is shortened to 0.83 times of the original distance, wherein a position represented by the new coordinates of each reference body surface feature point B2 is the target position of the reference body surface feature point B2.

For another example, assuming that the width of the neck of the user is 0.15 meters, and the second distance between two adjacent corresponding reference body surface feature points B2 characterizing the width of the neck of the reference three-dimensional human body model is 0.16 meters. After dividing the width of the neck by the second distance, the quotient obtained is approximately equal to 0.94, therefore 0.94 may be used as the width scaling ratio.

Then, the determining the target positions of two adjacent reference body surface feature points B2 for characterizing the width of the neck of the reference three-dimensional human body model includes: determining new coordinates of the two adjacent reference body surface feature points B2 so that a distance connecting two adjacent reference body surface feature points B2 with the new coordinates is shortened to 0.94 times of the original, wherein a position represented by the new coordinates of each reference body surface feature point B2 is the target position of the reference body surface feature point B2.

Optionally, in at least one of steps S204 to S209, the display unit 503 of the electronic device 500 may display the body image of the user and/or the body surface feature points B3 on the body image.

Optionally, in at least one of steps S204 to S209, the display unit 503 of the electronic device 500 may display the reference three-dimensional human body model.

At step S210: each reference body surface feature point B2 and each reference bone point A2 in the reference three-dimensional human body model are adjusted/moved to corresponding target positions, respectively, to obtain the customized three-dimensional human body model of the user.

Figure 6:
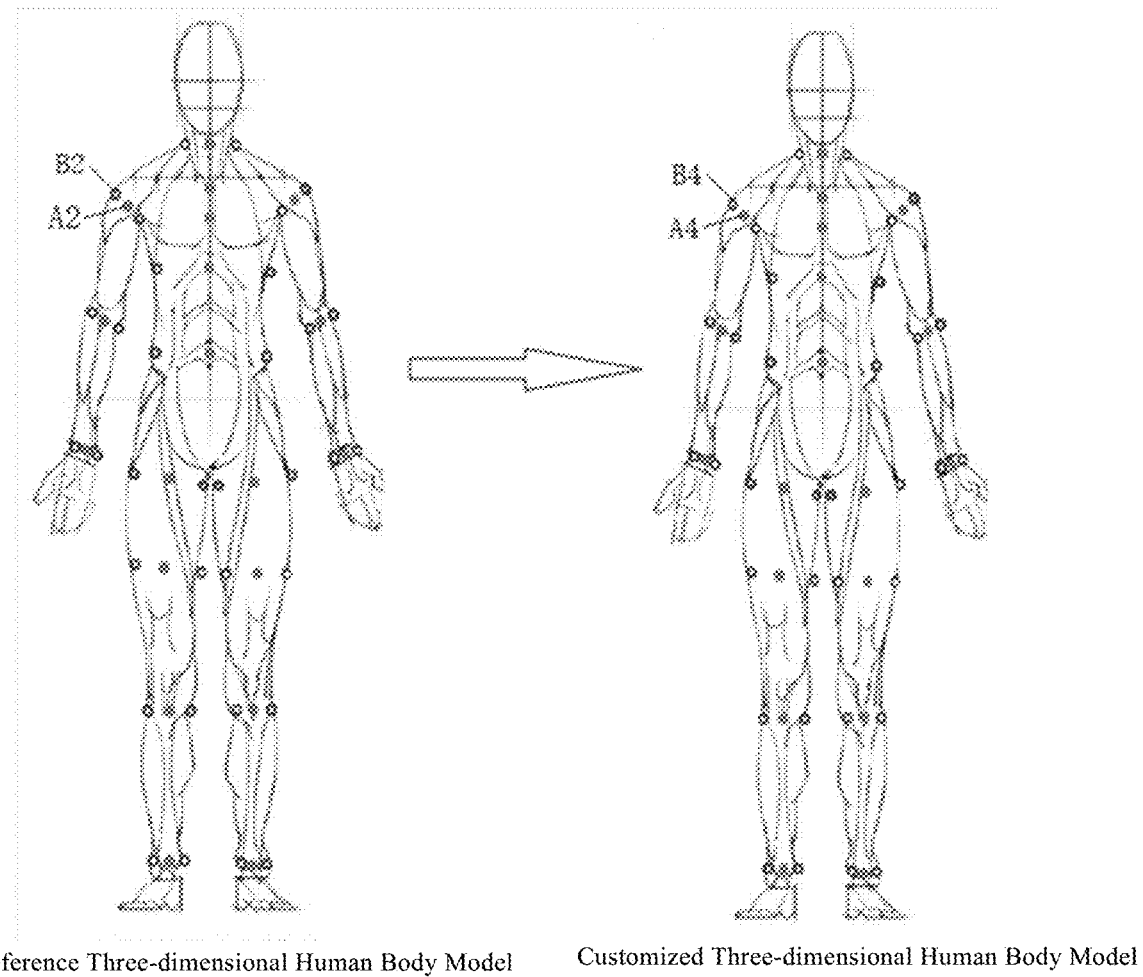
FIG. 6 is a schematic diagram of converting a reference three-dimensional human body model into a customized three-dimensional human body model, according to an embodiment of the present disclosure.

As shown in FIG. 6, each reference body surface feature point B2 and each reference bone point A2 in the reference three-dimensional human body model are adjusted to the corresponding target positions, respectively, to obtain a customized body surface feature point B4 and a customized reference bone point A4 in a customized three-dimensional human body model.

In steps S208 and S209, the coordinates in the three-dimensional coordinate system of the target positions of the reference body surface feature points B2 and the reference bone point A2 in each set of reference control points of the reference three-dimensional human body model have been determined. In step S210, the current coordinates of each reference body surface feature point B2 and each reference bone point A2 are adjusted to the coordinates of the corresponding target positions, so that each reference body surface feature point B2 and each reference bone point A2 are moved to the corresponding target positions.

In an embodiment, when the reference body surface feature points B2 and the reference bone point A2 in each set of reference control points of the reference three-dimensional human body model are moved in the height direction, by considering each set of reference control points as a unit, the reference body surface feature points B2 and the reference bone point A2 in each set of reference control points are moved simultaneously in the height direction to the corresponding target positions.

In an embodiment, when the reference body surface feature points B2 and the reference bone point A2 in each set of reference control points of the reference three-dimensional human body model are moved in the direction of the width of the body part, the position of the reference bone point A2 in each set of reference control points is kept unchanged, while the two reference body surface feature points B2 symmetrically distributed on both sides of the reference bone point A2 are scaled in the width direction of the body part to the corresponding target positions on both sides, respectively.

Optionally, in step S205, the display unit 503 of the electronic device 500 may display the reference three-dimensional human body model and the customized three-dimensional human body model.

In the process of performing steps S204 to S210, the position information of the actual body surface feature points of the human body image of the user is automatically recognized firstly, and then, according to the position information of the actual body surface feature points of the human body image of the user, the positions of the reference body surface feature points and the reference bone points of the reference three-dimensional human body model are adjusted more accurately, so that the reference three-dimensional human body model is further closer to the real body shape characteristic of the user, and finally a customized three-dimensional human body model having a higher matching degree with the user's real body shape is generated, thereby improving the reality of the customized three-dimensional human body model.

After step S210 is performed, the modeling method for a three-dimensional human body model provided by the embodiment of the present disclosure completes. Alternatively, after step S210 is performed, proceed to step S211.

At step S211: whether the body part of the user has an abnormal figure is determined according to a standard figure information of a body part of the user and the customized three-dimensional human body model of the user; and if an abnormal figure exists, abnormal figure information about the body part of the user is displayed.

It should be noted that the body parts of the user include at least the head, back, shoulders, spine, pelvis, legs and knees, etc. Abnormal figures include at least obesity, shortness, forward head, head tilt, kyphosis, uneven shoulders, scoliosis, pelvic tilt, knee hyperextension, O-shaped legs, X-shaped legs, etc.

Taking waistline as an example, according to Chinese male/female standard data (for example, the threshold range of chest circumference, waistline, and hipline) and the three-dimensional human body model of the user, it is determined whether the user is obese, and if so, obesity information of the user's waist is displayed.

Taking the spine as an example, according to the reference spine information of the spine and the customized three-dimensional human body model of the user, it is determined whether the user's spine has scoliosis, and if so, the scoliosis information of the user's spine is displayed. The scoliosis information may be the severity level of the scoliosis, the scoliosis angle information of the spin, and the like.

Taking the shoulders as an example, according to the reference figure information of the shoulders and the customized three-dimensional human body model of the user, it is determined whether the two shoulders of the user have a problem of uneven shoulders, and if so, uneven shoulder information of the user's shoulders is displayed. The uneven shoulder information may be the severity level of the uneven shoulder, the inclination angle information of the uneven shoulder, and the like.

In an embodiment, at least one of the waistline, hipline, chest circumference, and positional relationships between customized bone points of the customized human body model of the user is compared with a corresponding one of the waistline, hipline, chest circumference, and positional relationships between reference bone points of the reference human body model, wherein where the waistline, hipline, and chest circumference of the reference human body model reflect a threshold range of a standard waistline, a threshold range of a standard hipline, and a threshold of a standard chest circumference of the human body, and the positional relationship between the reference bone points of the reference human body model can reflect the standard skeleton structure of the human body.

In an embodiment of the present disclosure, a manner for displaying the abnormal figure information of the user's body part may at least include: the electronic device 500 displaying the abnormal figure information in graphics and text, or the electronic device 500 playing the abnormal figure information in voice.

Optionally, when the electronic device 500 displays the abnormal figure information in graphics and text, the abnormal figure information and the customized three-dimensional human body model can be displayed on the same interface. For example, the abnormal figure information is displayed on the periphery of the customized three-dimensional human body model.

Optionally, when the electronic device 500 displays the abnormal figure information in graphics and text, the abnormal figure information may also be separately displayed in an interface.

It should be noted that the determination process of whether other body parts have an abnormal figure can be similar to the determination process of the spine and shoulders described above, and will not be repeated here.

The present disclosure uses a customized three-dimensional human body model to characterize the of the real human body feature of a user, and recognizes whether the user has an abnormal figure by determining whether the customized three-dimensional human body model has an abnormal figure. The detection process can be performed by the electronic device 500 itself, and the detection of abnormal figure can be performed without the participation of professionals, which is helpful for the popularization and use of the technology. The detection operation of the electronic device 500 can improve the detection efficiency of abnormal figure, reduce the interference of subjective factors in the process of manually detecting abnormal figure, and help improve the detection accuracy.

In an embodiment of the present disclosure, step S211 includes steps b1 and b2.

At step b1, the reference positional relationship between the body surface feature points and/or bone points of a body part is compared with the actual positional relationship between the customized body surface feature points B4 and/or the customized bone points A4 in the customized three-dimensional human body model of the user, to obtain a comparison result.

The reference figure information of the body part may include: the reference positional relationship between the body surface feature points and/or the bone points characterizing the specific body part in step (b1).

Taking the spine as an example, the reference figure information of the spine may be a reference positional relationship between bone points in the spine.

Specifically, the reference positional relationship between the bone points in the spine can be reflected by the bending angle of the line connecting the bone points in the spine. The bending angle of the line connecting the bone points in the spine can be recorded as a reference spine bending angle, and the reference spine bending angle can be used as the reference figure information of the spine. A reference spine bending angle can be an angle range, or it can be a specific angle value.

The bending angle of the line connecting the bone points in the reference spine is compared with the bending angle of the line connecting the customized bone points A4 in the spine in the customized three-dimensional human body model of the user, to obtain a comparison result.

At step b2, whether a specific body part of the user has an abnormal figure is determined according to the comparison result.

Taking the spine as an example, if the comparison result is "the bending angle of the line connecting the customized bone points A4 in the spine in the customized three-dimensional human body model of the user exceeds the range of the reference spine bending angle", it is determined that the user's spine has the problem of scoliosis; if the comparison result is "the bending angle of the line connecting the customized bone points A4 in the spine in the customized three-dimensional human body model of the user does not exceed the range of the reference spine bending angle", it is determined that the user's spine does not have the problem of scoliosis.

In an embodiment, step S211 includes:
  comparing at least one of the waistline, the hipline, and the chest circumference of the body parts in the three-dimensional human body model of the user with the corresponding one of the standard waistline, the standard hipline, and the standard chest circumference of a Chinese male/female, to obtain a comparison result.

If the comparison result is "the waistline of the customized three-dimensional human body model of the user exceeds the standard size of the waistline of a Chinese male/female", it is determined that the user has a problem of obesity; if the comparison result is "the waistline of the customized three-dimensional human body model of the user does not exceed the standard size of the waistline of a Chinese male/female", it is determined that the user does not have the problem of obesity.

In an embodiment of the present disclosure, after determining that a body part of the user has an abnormal figure according to the comparison result, the severity level of the abnormal figure of the body part may be continuously determined. For example, a bending angle of a line connecting the customized bone points A4 in the spine in the customized three-dimensional human body model of the user is subtracted from a reference spine bending angle to obtain a difference, and the severity level of scoliosis is determined according to the obtained difference.

The above steps (b1) and (b2), taking the spine as an example, give a more specific exemplary introduction to the determination process of whether a body part has an abnormal figure. A determination process of whether other body parts has an abnormal figure can be similar to the determination process for the spine described above, and will not be repeated here.

After step S211 is performed, the modeling method for a three-dimensional human body model provided by the embodiment of the present disclosure can be ended. Alternatively, after step S211 is performed, proceed to step S212.

At step S212: health advice information corresponding to the abnormal figure information is displayed according to the body part of the user with the abnormal figure and the abnormal figure information.

In an embodiment of the present disclosure, an advice information library stores health advice information therein, and body parts have a mapping relationship with the health suggestion information. When it is determined that a certain body part of the user has an abnormal figure, advice information corresponding to the abnormal figure is invoked from the advice information library according to the mapping relationship, and is displayed by the electronic device 500.

In an embodiment of the present disclosure, the severity level of an abnormal figure of a body part may also be determined. There is a mapping relationship between the body parts, the severity levels of the abnormal figures and the health advice information. When it is determined that a specific body part of the user has an abnormal figure, and a severity level of the abnormal figure is also determined, advice information corresponding to the abnormal figure is invoked from the advice information library according to the mapping relationship, and is displayed by the electronic device 500.

In an embodiment of the present disclosure, a manner for displaying the health advice information may at least include: the electronic device 500 displaying the health advice information in graphics and text, or the electronic device 500 playing the health advice information in voice.

Optionally, when the electronic device 500 displays the health advice information in graphics and text, the health advice information and the customized three-dimensional human body model can be displayed on the same interface. For example, the health advice information is displayed on the periphery of the customized three-dimensional human body model.

Optionally, when the electronic device 500 displays the health advice information in graphics and text, the health advice information may also be separately displayed in an interface.

Figure 7:
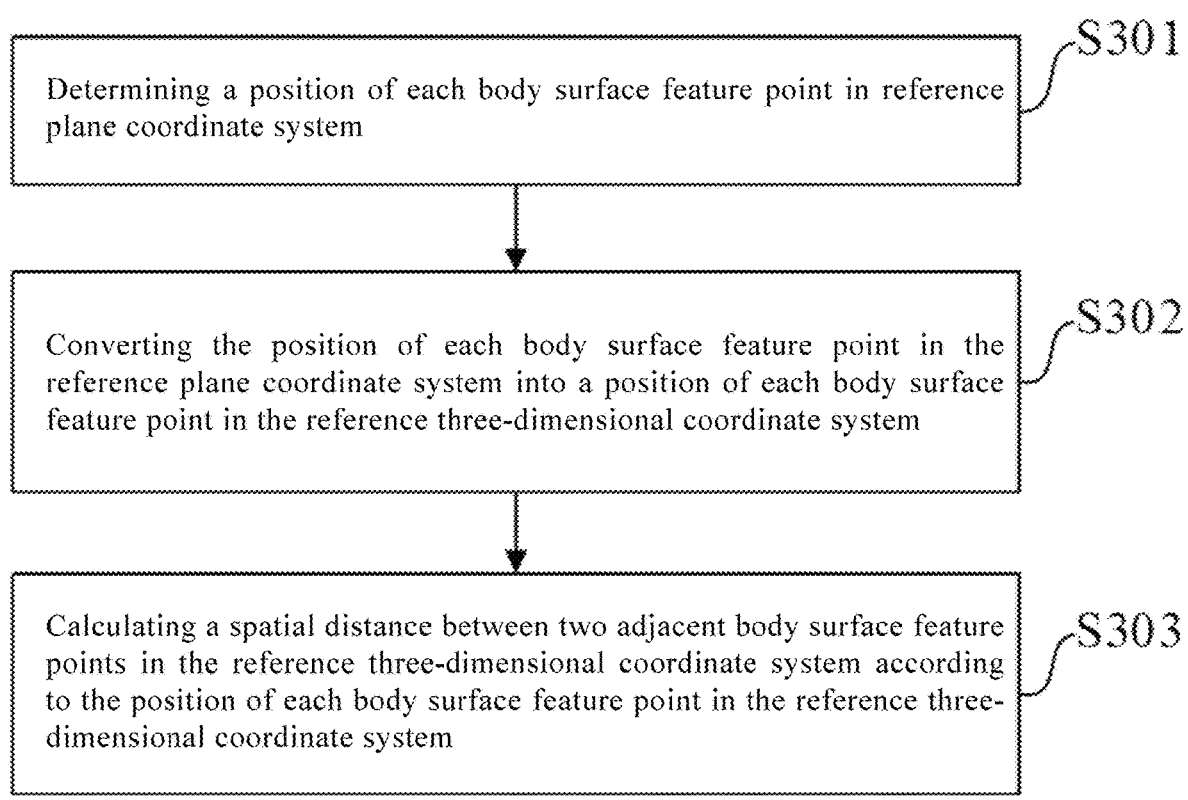
FIG. 7 is a schematic diagram of steps of determining spatial distances of body surface feature points in a reference three-dimensional coordinate system, according to an embodiment of the present disclosure.

An embodiment of the present application also provides an expansion method of step S206 (that is, calculating the spatial distance of each pair of associated actual body surface feature points B3 in the three-dimensional coordinate system). The flowchart of the expansion method is shown in FIG. 7, and includes steps S301 to S303.

At step S301, a position of each body surface feature point B3 of the human body image of a user in the plane coordinate system is determined.

The reference plane coordinate system may be established on the two-dimensional plane of the human body image of the user, and the position of each body surface feature point B3 of the human body image of the user in the plane coordinate system may be represented by two-dimensional coordinates.

At step S302: the position of each body surface feature point B3 in the plane coordinate system is converted into a position of each body surface feature point B3 in the three-dimensional coordinate system. In an embodiment of the present disclosure, step S302 includes steps b1 and b2.

At step b1, a reference distance is determined according to an actual human body size of the user.

In an embodiment of the present disclosure, the user's height value is used as the actual human body size, and the reference distance is determined according to the height value.

At step b2, the position of each body surface feature point B3 in the three-dimensional coordinate system is determined according to the reference distance and the position of each body surface feature point B3 in the plane coordinate system.

The position of each body surface feature point B3 in the plane coordinate system is represented by two-dimensional coordinates. According to the reference distance, the two-dimensional coordinates of the position of the body surface feature point B3 in the plane coordinate system may be converted into the coordinates of each body surface feature point B3 in the three-dimensional coordinate system.

When a short user is photographed at a close distance, the user in the captured photo looks taller. When a tall user is taken at a long distance, the user in the captured photo looks shorter.

Therefore, in the conversion process between the two-dimensional coordinate system and the three-dimensional coordinate system, the reference distance needs to be used. The reference distance is a reference basis for the coordinate system conversion. In an embodiment, the reference distance is the height of the user.

At step S303: a spatial distance between each pair of associated body surface feature points B3 in the three-dimensional coordinate system is calculated according to the position of each body surface feature point B3 in the three-dimensional coordinate system.

The position of a body surface feature point B3 in the three-dimensional plane coordinate system may be represented by the three-dimensional coordinates of the body surface feature point B3 in the three-dimensional plane coordinate system. According to the three-dimensional coordinates of each pair of associated body surface feature points B3 in the three-dimensional coordinate system, the spatial distance between the two body surface feature points B3 in the three-dimensional coordinate system may be calculated.

Figure 8:
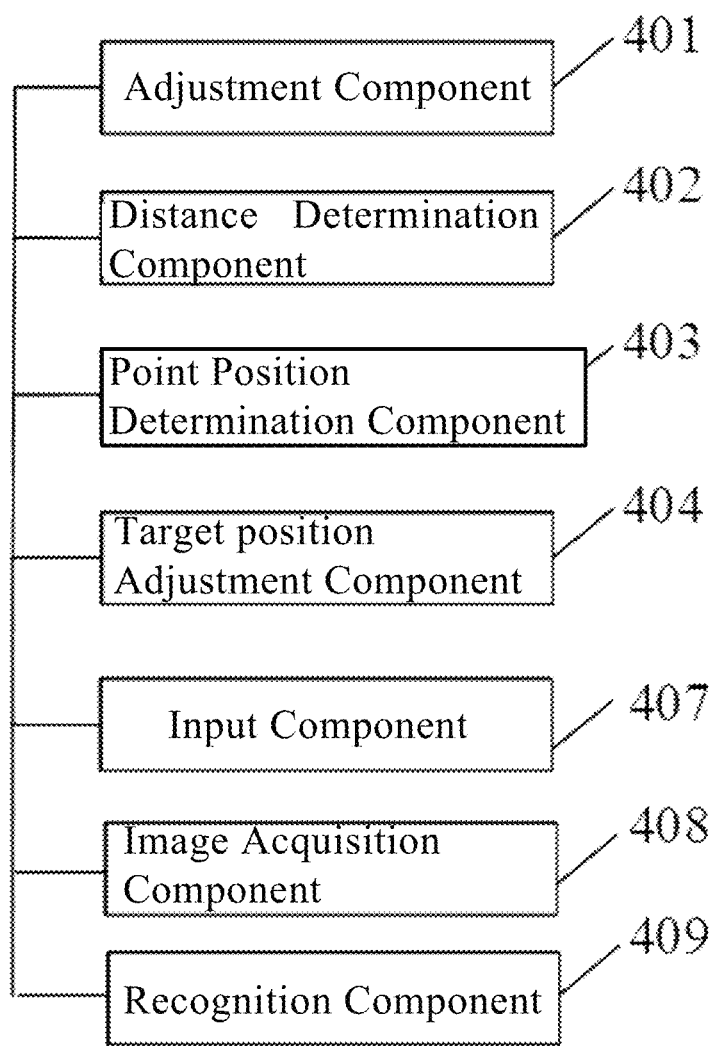
FIG. 8 is a block diagram of a modeling device for a three-dimensional human body model according to an embodiment of the present disclosure.

An embodiment of the present disclosure provides a modeling device 400 for a three-dimensional human body model. As shown in FIG. 8, the modeling device 400 includes an adjustment component 401, a distance determination component 402, a point position determination component 403, a target position adjustment component 404, an input component 407, an image acquisition component 408 and a recognition component 409. The adjustment component 401, the distance determination component 402, the point position determination component 403, and the target position adjustment component 404 are modeling components.

The input component 407 is configured to obtain the human body size of the user.

The adjustment component 401 is configured to perform a scaling process on the standard three-dimensional human body model according to the human body size, to obtain a three-dimensional human body model matching the human body size of the user. The reference three-dimensional human body model has multiple reference body surface feature points marked on the human body surface and multiple reference bone points marked on the human skeleton. The multiple reference body surface feature points and the multiple reference bone points are divided into multiple sets of control points. Each set of control points includes two reference body surface feature points and one reference bone point arranged in the width direction of a body part.

The image acquisition component 408 is configured to acquire a human body image of the user.

The distance determination component 402 is configured to obtain the size of a body part of the user according to the human body image. The human body image has multiple body surface feature points marked on the human body surface. Each pair of associated body surface feature points B3 may characterize the body part of the user.

The point position determination component 403 is configured to determine, according to the size of the body part of the user, target positions to which each reference body surface feature point B2 and the reference bone point A2 in each set of control points of the reference three-dimensional human body model will be adjusted.

The target position adjustment component 404 is configured to adjust each reference body surface feature point B2 and each reference bone point A2 in the reference three-dimensional human body model to corresponding target positions, to obtain a customized three-dimensional human body model of the user.

In an embodiment of the present disclosure, the input component 407 is further configured to acquire a height value of the user as a human body size. The adjusting component 401 determines a height scaling ratio according to the height value and a height value of the standard three-dimensional human body model; perform a scaling process on the standard three-dimensional human body model according to the height scaling ratio to obtain a reference three-dimensional human body model matching the human body height feature of the user.

In an embodiment of the present disclosure, the adjustment component 401 is further configured to: according to the height scaling ratio, perform a scaling process on a distance between standard body surface feature points B1 that are adjacent (e.g., immediately adjacent) in the vertical direction in the standard three-dimensional human body model and perform a scaling process on a distance between standard bone points A1 that are adjacent (e.g., immediately adjacent) in the vertical direction; use the scaled standard three-dimensional human body model as the reference three-dimensional human body model, wherein the standard body surface feature points B1 serve as the reference body surface feature points B2, and the standard bone points A1 serve as the standard bone points A2.

In an embodiment of the present disclosure, the adjustment component 401 is further configured to: before the standard three-dimensional human body model is scaled according to the human body size, according to user's category information, acquire from the three-dimensional human body model library a standard three-dimensional body model matching the category information; the category information includes at least one of gender, race, and age.

In an embodiment of the present disclosure, the recognition component 409 recognize multiple body surface feature points B3 in the human body image through image recognition; the distance determination component 402 calculates a spatial distance between each pair of associated body surface feature points B3 in the three-dimensional coordinate system as the size of a body part of the user.

In an embodiment of the present disclosure, the distance determination component 402 is further configured to: determine a position of each body surface feature point B3 in the plane coordinate system; convert the position of each body surface feature point B3 in the plane coordinate system into a position of each body surface feature point B3 in the three-dimensional coordinate system according to the height of the user; calculate a spatial distance between each pair of associated body surface feature points B3 in the three-dimensional coordinate system according to the position of each body surface feature point B3 in the three-dimensional coordinate system.

In an embodiment of the present disclosure, the distance determination component 402 is further configured to: determine a reference distance according to the human body size of the user; determine the position of each body surface feature point B3 in the three-dimensional coordinate system according to the reference distance and the position of each body surface feature point B3 in the plane coordinate system.

In an embodiment of the present disclosure, the point determination component 403 is further configured to: determine a length scaling ratio of each pair of associated reference body surface feature points B2 according to a length of a body part of the user and a first distance between a pair of associated reference body surface feature points B2 corresponding to each pair of associated body surface feature points B3; determine target positions to which each set of reference control points will be moved according to the length scaling ratio of each pair of associated reference body surface feature points B2; or alternatively, The point position determination component 403 is further configured to: for each set of control points, according to a position of the reference bone point and a positional relationship between the reference bone point and the reference body surface feature points, determine a target position in the width direction of the body part to which each reference body surface feature point in the set of control points will be moved to.

In an embodiment of the present disclosure, the point position determination component 403 is further configured to: divide a width of a body part of the user by a second distance between two adjacent reference body surface feature points for characterizing the width of the same body part in the reference three-dimensional human body model, to obtain a width scaling ratio of the two adjacent reference body surface feature points for characterizing the width of the body part; keep a position of each reference bone point unchanged, and determine target positions to which the two reference body surface feature points symmetrically distributed on both sides of the reference bone point will be moved in the width direction of the body part, according to the width scaling ratio.

Figure 9:
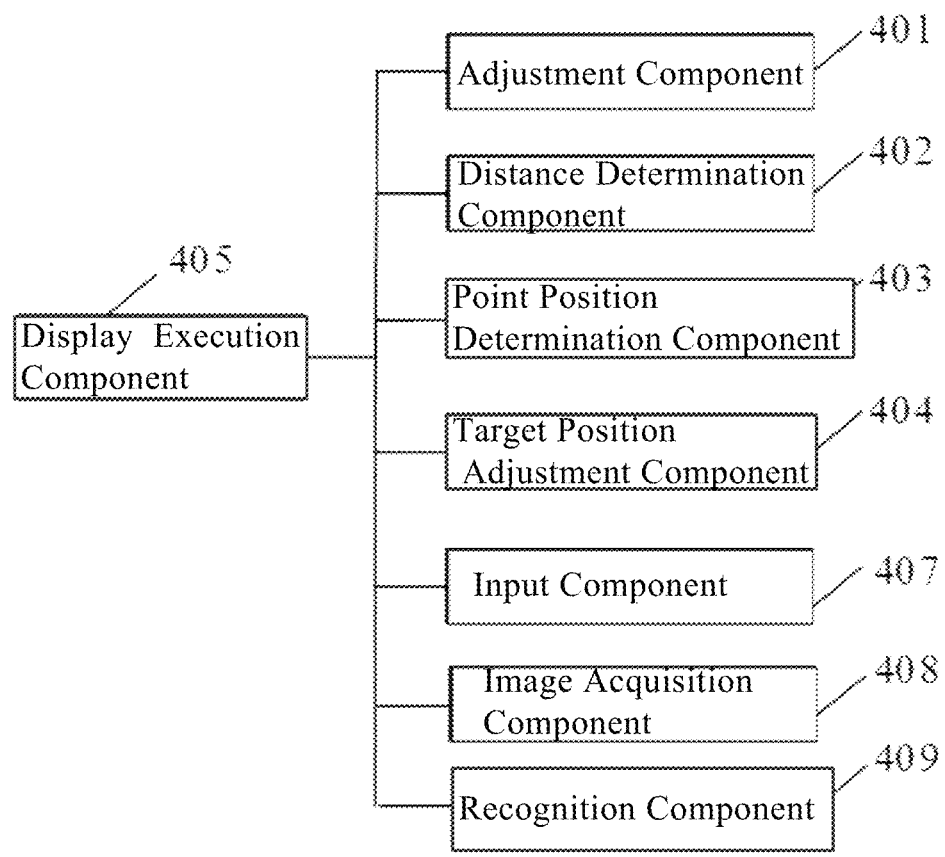
FIG. 9 is a block diagram of a modeling device for a three-dimensional human body model according to an embodiment of the present disclosure.

An embodiment of the present disclosure also provides a modeling device 400 for a three-dimensional human body model. As shown in FIG. 9, in addition to the aforementioned adjustment component 401, distance determination component 402, point position determination component 403, target position adjustment component 404, input component 407, image acquisition component 408, and recognition component 409, the modeling device 400 further includes a display execution component 405. The display execution component 405 is configured to control the display unit 503 to display at least one of a standard three-dimensional human body model, a human body image, a reference three-dimensional human body model, and a customized three-dimensional human body model.

Figure 10:
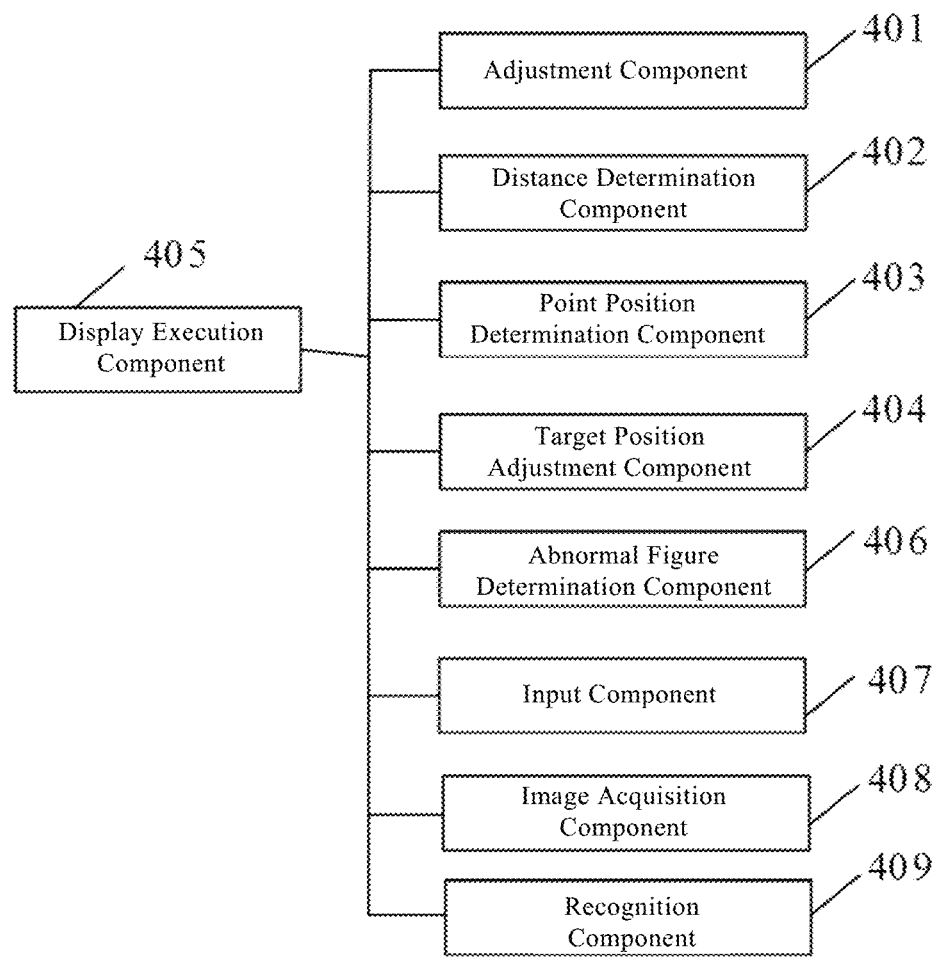
FIG. 10 is a block diagram of a modeling device for a three-dimensional human body model according to an embodiment of the present disclosure.

An embodiment of the present disclosure also provides another modeling device 400 for a three-dimensional human body model. As shown in FIG. 10, in addition to the aforementioned adjustment component 401, distance determination component 402, point position determination component 403, target position adjustment component 404, display execution component 405, input component 407, image acquisition component 408, and recognition component 409, the modeling device 400 further includes an abnormal figure determination component 406.

The abnormal figure determination component 406 is configured to: determine whether a body part of the user has an abnormal figure according to reference figure information of the body part and a customized three-dimensional human body model of the user, and if so, display abnormal figure information of the body part of the user.

The abnormal figure determination component 406 is further configured to: compare standard positional relationship between body surface feature points and/or bone points in the body part with actual positional relationship between customized body surface feature points B4 and/or customized bone points in the customized three-dimensional human body model of the user, to obtain a comparison result, and determine whether the body part of the user has an abnormal figure according to the comparison result.

The abnormal figure determination component 406 is further configured to: display corresponding health advice information according to the body part of the user with abnormal figure and according to the abnormal figure information.

The modeling devices 400 for a three-dimensional human body model provided by the embodiments of the present disclosure have the same inventive concept and the same beneficial effects as the modeling methods for a three-dimensional human body model in the aforementioned embodiments. The content of the modeling device 400 for a three-dimensional human body model not shown in detail may refer to the aforementioned embodiments, which will not be repeated here.

Figure 11:
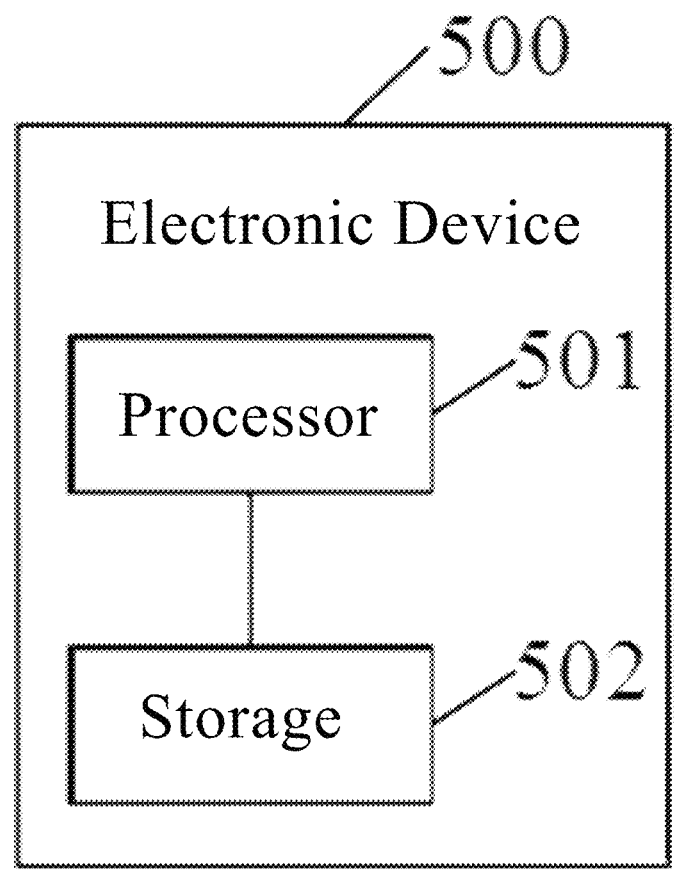
FIG. 11 is a block diagram of an electronic device according to an embodiment of the present disclosure.

Based on the same inventive concept, an embodiment of the present disclosure further provides an electronic device 500. As shown in FIG. 11, the electronic device 500 includes a processor 501 and a storage 502.

The storage 502 is configured to store machine-readable instructions which, when executed by the processor 501, cause the processor 501 to execute the modeling method for a human body model according to any one of the above embodiments of the present disclosure.

Optionally, the electronic device 500 further includes a bus and a communication unit, and the processor 501, the storage 502, and the communication unit are all electrically connected to the bus.

The processor 501 can be a CPU (Central Processing Unit), a general-purpose processor, a DSP (Digital Signal Processor), an ASIC (Application Specific Integrated Circuit), an FPGA (Field-Programmable Gate) Array) or other programmable logic devices, transistor logic devices, hardware components or any combination thereof. It can implement or execute various exemplary logical blocks, components and circuits described in conjunction with the content of the present disclosure. The processor 501 can also be a combination that implements computing functions, for example, including a combination of one or more microprocessors, a combination of a DSP and a microprocessor, and so on.

The storage 502 can be a ROM (Read-Only Memory) or other types of static storage devices that can store static information and instructions, a RAM (Random Access Memory) or other types of dynamic storage devices that can store information and instructions, or can be an EEPROM (Electrically Erasable Programmable Read Only Memory), a CD-ROM (Compact Disc Read-Only Memory) or other optical disk storage, an optical disc storage (including a compact disc, laser disc, optical disc, digital versatile disc, Blu-ray disc, etc.), a magnetic disk storage medium or other magnetic storage devices, or any other medium which can be used to carry or store desired program codes in the form of instructions or data structures and can be accessed by a computer, but which is not limited to this.

Figure 12:
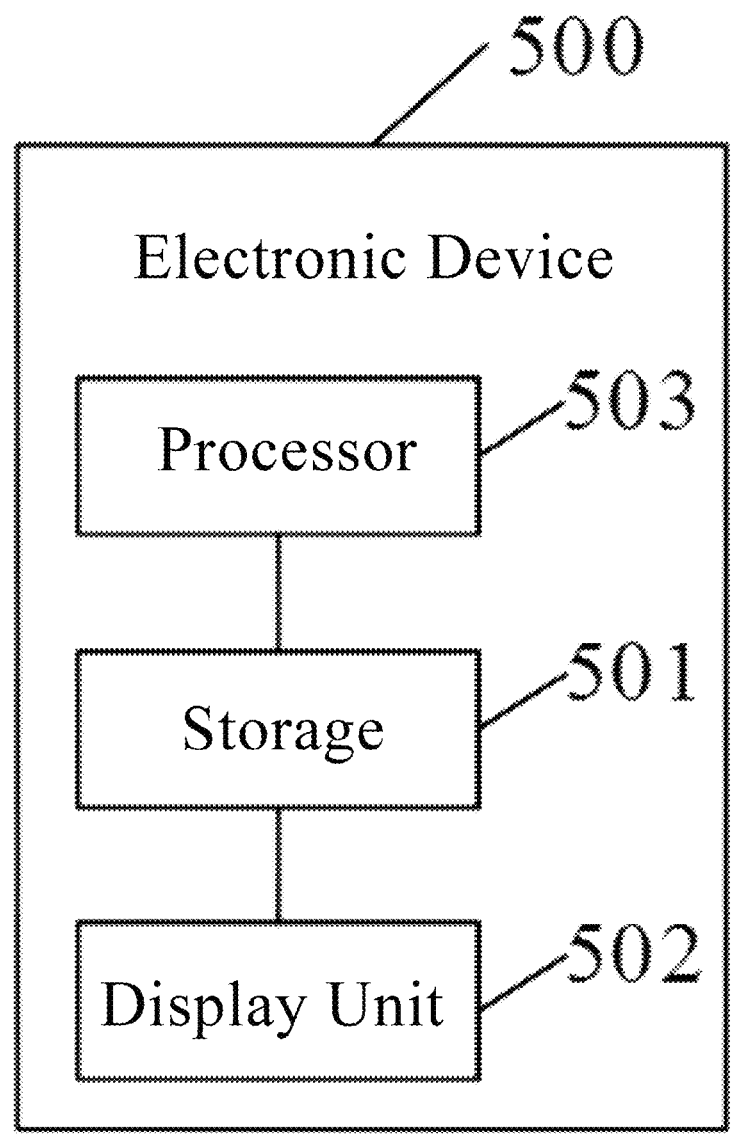
FIG. 12 is a block diagram of an electronic device according to an embodiment of the present disclosure.

An embodiment of the present disclosure further provides another electronic device 500. As shown in FIG. 12, the electronic device 500 includes a display unit 503 in addition to the aforementioned processor 501, storage 502, bus, and communication unit.

The display unit 503 is electrically connected to the processor 501, and the display unit 503 is configured to display at least one of a standard three-dimensional human body model, a human body image, a reference three-dimensional human body model, and a customized three-dimensional human body model.

Optionally, the electronic device 500 has an information input unit, and the human body size (such as a height value) of the user is input through the input unit, so that the electronic device 500 can acquire the human body size of the user. The input mode supported by the information input unit of the electronic device 500 can be determined according to actual design needs, such as supporting for touch input or voice input, etc. The specific type of the information input unit will be further introduced in the subsequent content.

The electronic device provided by the embodiments of the present disclosure may be a mobile phone, a tablet computer, a wearable device, a vehicle-mounted device, an augmented reality (AR)/virtual reality (VR) device, a laptop, an ultra-mobile personal computer (UMPC), a netbook, a personal digital assistant (PDA), and so on. The specific types of display devices are not limited in the embodiments of the present disclosure.

The electronic device 500 provided by the embodiment of the present disclosure has the same inventive concept and the same beneficial effects as the modeling methods for a three-dimensional human body model in the aforementioned embodiments. The content of the electronic device 500 not shown in detail may refer to the aforementioned embodiments, which will not be repeated here.

Based on the same inventive concept, an embodiment of the present disclosure further provides a computer-readable storage medium with a computer program stored thereon, when executed by a processor, the computer program implementing the modeling method for a human body model according to any one of the aforementioned embodiments of the present disclosure.

The computer-readable medium includes, but is not limited to, any type of disk (including floppy disk, hard disk, optical disk, CD-ROM, and magneto-optical disk), a ROM, a RAM, an EPROM (Erasable Programmable Read-Only Memory), an EEPROM, a flash memory, a magnetic card or light card. That is, the readable medium includes any medium that stores or transmits information in a readable form by a device (for example, a computer).

The embodiments of the present disclosure, when applied, have at least the following beneficial effects:

1. In the embodiments of the present disclosure, in the process of executing the modeling methods for a human body model of the present disclosure, on the basis of a standard three-dimensional human body model, the standard three-dimensional human body model is automatically scaled according to the human body size of a user, to generate a reference three-dimensional human body model similar to the body shape of the user.

Therefore, the positions of the feature points and the positions the bone points of the standard three-dimensional human body model can match their desired target positions, which reduces the amount of calculation in subsequent steps and helps to increase the process speed.

After that, position information of the body surface feature points of the human body image of the user is automatically recognized, and the reference three-dimensional human body model is adjusted more accurately according to the position information of the body surface feature points of the human body image of the user, so that the reference three-dimensional human body model is further closer to the user's real body shape characteristic to finally generate a customized three-dimensional human body model matching the user's real body shape.

According to the modeling methods of the present disclosure, since the reference bone points of the reference three-dimensional human body model are only scaled in the height direction, and not in the width direction of the body part, the method can generate a three-dimensional human body model having the same figure as the standard three-dimensional human body model.

The aforementioned modeling methods for a three-dimensional human body model can be executed by the electronic device itself. Compared with the manual modeling methods, the modeling methods of the present disclosure is faster and more efficient, and the generated three-dimensional human body model has a higher matching degree with the user's body shape.

2. In the embodiments of the present disclosure, a customized three-dimensional human body model may characterize the feature of the real human body of a user. By determining whether the customized three-dimensional human body model has an abnormal figure, whether the user has an abnormal figure can be recognized. The detection process can be performed by the electronic device itself, and the detection of abnormal figure can be performed without the participation of professionals, which is helpful for the popularization and use of technology. The detection operation of electronic device can improve the detection efficiency of abnormal figure, reduce the interference of subjective factors in the process of manually detecting abnormal figure, and help to improve the accuracy of detection.

It will be appreciated that the above implementations are merely exemplary implementations used to illustrate the principle of the present disclosure, and the present disclosure is not limited thereto. For those of ordinary skill in the art, various modifications and improvements can be made without departing from the spirit and essence of the present disclosure, and these modifications and improvements are also regarded as the protection scope of the present disclosure.

What is claimed is:

1. A modeling method for a human body model, comprising:
    obtaining a customized human body model customized for a user by modeling;
    comparing standard figure information of a body part with figure information of the same body part in the customized human body model of the user to determine whether in the body part of the user has an abnormal figure;

displaying information about the abnormal figure of the body part of the user, in response to a presence of an abnormal figure, wherein obtaining the customized human body model customized for the user by modeling comprises:

acquiring a human body size of the user;

performing a scaling process on a standard human body model according to the human body size, to obtain a reference human body model matching the human body size of the user, the reference human body model having multiple reference body surface feature points marked on a human body surface and multiple reference bone points marked on a human skeleton, and the multiple reference body surface feature points and the multiple reference bone points being divided into multiple sets of reference control points, each set of reference control points comprising two of the reference body surface feature points and one of the reference bone points that are arranged in a width direction of a body part;

acquiring a human body image of the user;

obtaining sizes of body parts of the user according to the human body image;

determining to-be-moved target positions of each reference body surface feature point and the reference bone point of each set of reference control points of the reference human body model, according to the sizes of the body parts of the user; and adjusting each reference body surface feature point and each reference bone point of the reference human body model to the to-be-moved target positions to obtain the customized human body model of the user.

2. The modeling method of claim 1, wherein:

the customized human body model of the user has multiple customized body surface feature points marked on a human body surface and multiple customized bone points marked on a human skeleton, and comparing the standard figure information of the body part with the figure information of the same body part in the customized human body model of the user to determine whether the body part of the user has an abnormal figure, comprises:

comparing at least one of a waistline, a hipline, a chest circumference, and a bending angle of the multiple customized bone points of the customized human body model of the user with a corresponding one of a threshold range of a standard waistline, a threshold range of a standard hipline, a threshold range of a standard chest circumference, and a standard bending angle of skeleton, to obtain a comparison result;

determining whether the body part of the user has an abnormal figure according to the comparison result.

3. The modeling method of claim 1, wherein:

the comparing the standard figure information of the body part with the figure information of the same body part in the customized human body model of the user to determine whether the body part of the user has an abnormal figure, comprises:

providing a reference human body model which has multiple reference body surface feature points marked on a human body surface and multiple reference bone points marked on a human skeleton;

comparing at least one of a waistline, a hipline, a chest circumference, and positional relationship between customized bone points of the customized human body model of the user with a corresponding one of a waistline, a hipline, a chest circumference, and positional relationship between reference bone points of the reference human body model, to obtain a comparison result, wherein the waistline, the hipline, and the chest circumference of the reference human body model indicate a threshold range of a standard waist circumstance, a threshold range of a standard hip circumstance, and a threshold range of a standard chest circumstance of a human body, respectively, and the positional relationship between the reference bone points of the reference human body model indicates a standard skeleton structure of the human body;

determining whether the body part of the user has an abnormal figure according to the comparison result.

4. The modeling method of claim 1, wherein, the abnormal figure of the body part comprises at least one of obesity, shortness, forward head, head tilt, kyphosis, uneven shoulders, scoliosis, pelvic tilt, knee hyperextension, O-shaped legs, and X-shaped legs.

5. The modeling method of claim 1, wherein, after the displaying information about the abnormal figure of the body part of the user, the method further comprises:

displaying health advice information corresponding to the abnormal figure according to the abnormal figure of the body part of the user.

6. The modeling method of claim 1, wherein, the human body size of the user is a height value of the user;

performing a scaling process on the standard human body model according to the human body size to obtain the reference human body model matching the human body size of the user, comprises:

determine a height scaling ratio according to the height value of the user and a height value of the standard human body model;

performing a scaling process on the standard human body model in a vertical direction according to the height scaling ratio, to obtain the reference human body model having a height value equal to the height value of the user.

7. The modeling method of claim 6, wherein, the height scaling ratio is a quotient obtained by dividing the height value of the user by the height value of the standard human body model.

8. The modeling method of claim 7, wherein, the standard human body model has multiple standard body surface feature points marked on a human body surface and multiple standard bone points marked on a human skeleton, the multiple standard body surface feature points and the multiple standard bone points are divided into multiple sets of standard control points, each set of standard control points comprises two of the standard body surface feature points and one of the standard bone points that are arranged in a width direction of a body part, performing a scaling process on the standard human body model in the vertical direction according to the height scaling ratio to obtain the reference human body model having a height value equal to the height value of the user, comprises:

performing a scaling process on a distance between any two adjacent sets of standard control points in the vertical direction of the standard human body model according to the height scaling ratio to obtain the reference human body model, with the standard body surface feature points serving as the reference body surface feature points and the standard bone points serving as the reference bone points.

9. The modeling method of claim 6, wherein,
the standard human body model has multiple standard body surface feature points marked on a human body surface and multiple standard bone points marked on a human skeleton, the multiple standard body surface feature points and the multiple standard bone points are divided into multiple sets of standard control points, each set of standard control points comprises two of the standard body surface feature points and one of the standard bone points that are arranged in a width direction of a body part,
performing a scaling process on the standard human body model in the vertical direction according to the height scaling ratio to obtain the reference human body model having a height value equal to the height value of the user, comprises:
performing a scaling process on a distance between any two adjacent sets of standard control points in the vertical direction of the standard human body model according to the height scaling ratio to obtain the reference human body model, with the standard body surface feature points serving as the reference body surface feature points and the standard bone points serving as the reference bone points.

10. The modeling method of claim 1, wherein determining the to-be-moved target positions of each reference body surface feature point and the reference bone point of each set of reference control points of the reference human body model according to the sizes of the body parts of the user, comprises:
dividing a length of a body part of the user by a first distance between two adjacent reference body surface feature points of the reference three-dimensional human body model, the first distance characterizing the length of the same body part, to obtain a length scaling ratio of the two adjacent reference body surface feature points characterizing the length of the body part;
recognizing multiple body surface feature points in the human body image by using image recognition, wherein a midpoint of a line between two adjacent body surface feature points in a horizontal direction serves as a bone point of the human body image, the two adjacent body surface feature points representing a body part, and
determining, in the human body image of the user, a distance in the horizontal direction between two immediately adjacent bone points in a length direction of a same body part of the user;
dividing the distance in the horizontal direction by a length of the body part in the human body image of the user, to obtain a sine value representing deformation of the body part;
keeping unchanged a position of one reference bone point of the reference human body model corresponding to one bone point of the two immediately adjacent bone points of the human body image, and determining a to-be-moved target position of another reference bone point of the reference human body model corresponding to the other bone point of the two immediately adjacent bone points of the human body image according to the sine value and the length scaling ratio, wherein the multiple body surface feature points of the human body image are in one-to-one correspondence with the multiple reference body surface feature points of the reference human body model, and the multiple bone points of the human body image are in one-to-one correspondence with the multiple reference bone points of the reference human body model.

11. The modeling method of claim 1, wherein determining to-be-moved target positions of each reference body surface feature point and the reference bone point of each set of reference control points of the reference human body model according to the sizes of the body parts of the user, comprises:
dividing a width of a body part of the user by a second distance between two adjacent reference body surface feature points of the reference human body model, the second distance characterizing the width of the same body part, to obtain a width scaling ratio of the two adjacent reference body surface feature points characterizing the width of the body part;
keeping unchanged the to-be-moved target position of the reference bone point, and determining to-be-moved target positions, in the width direction of the body part, of two reference body surface feature points symmetrically distributed on either side of the reference bone point according to the width scaling ratio.

12. The modeling method of claim 1, wherein,
obtaining the sizes of the body parts of the user according to the human body image comprises:
recognizing multiple body surface feature points in the human body image by using image recognition;
calculating a spatial distance in three-dimensional coordinate system of two adjacent body surface feature points characterizing a size of a body part of the user among the multiple body surface feature points, as the size of the body part of the user.

13. The modeling method of claim 12, wherein calculating the spatial distance in the three-dimensional coordinate system of two adjacent body surface feature points characterizing a size of a body part of the user among the multiple body surface feature points as the size of the body part of the user, comprises:
establishing a plane coordinate system in the human body image of the user;
determining a position of each of the body surface feature points of the human body image in the plane coordinate system;
converting the position of each of the body surface feature points in the plane coordinate system into a position of each of the body surface feature points in the three-dimensional coordinate system according to a height of the user; and
calculating the spatial distance between the two adjacent body surface feature points in the three-dimensional coordinate system according to the position of each of the body surface feature points in the three-dimensional coordinate system.

14. The modeling method of claim 1, wherein, before performing the scaling process on the standard human body model according to the human body size, the method further comprises:
acquiring, in a database, a standard human body model matching category information of the user according to the category information of the user, the category information of the user comprising at least one of gender, race, and age.

15. The modeling method of claim 1, further comprising: displaying at least one of the standard human body model, the human body image, the reference human body model, and the customized human body model of the user.

16. An electronic device, comprising:
a processor; and
a storage configured to store machine-readable instructions which, when executed by the processor, cause the processor to execute the modeling method for a human body model according to claim 1.

17. The electronic device of claim 16, comprising:
a display unit electrically connected to the processor, and is configured to display at least one of a standard human body model, a human body image, a reference human body model, and a customized human body model of a user.

18. A non-transitory computer-readable storage medium with a computer program stored thereon, when executed by a processor, the computer program implementing the modeling method for a human body model according to claim 1.

19. A modeling device for a human body model, comprising:
a modeling component configured to obtain a customized human body model customized for a user by modeling;
an abnormal figure determination component configured to compare standard figure information of a body part with figure information of the same body part in the customized human body model of the user to determine whether the body part of the user has an abnormal figure;
a display unit configured to display information about the abnormal figure of the body part of the user, in response to a presence of an abnormal figure,
the modeling component is further configured to:
acquire a human body size of the user;
perform a scaling process on a standard human body model according to the human body size, to obtain a reference human body model matching the human body size of the user, the reference human body model having multiple reference body surface feature points marked on a human body surface and multiple reference bone points marked on a human skeleton, and the multiple reference body surface feature points and the multiple reference bone points being divided into multiple sets of reference control points, each set of reference control points comprising two of the reference body surface feature points and one of the reference bone points that are arranged in a width direction of a body part;
acquire a human body image of the user;
obtain sizes of body parts of the user according to the human body image;
determine to-be-moved target positions of each reference body surface feature point and the reference bone point of each set of reference control points of the reference human body model, according to the sizes of the body parts of the user; and
adjust each reference body surface feature point and each reference bone point of the reference human body model to the to-be-moved target positions to obtain the customized human body model of the user.

* * * * *